(12) United States Patent
Sato

(10) Patent No.: US 11,684,425 B2
(45) Date of Patent: Jun. 27, 2023

(54) X-RAY FLUOROSCOPIC IMAGING APPARATUS

(71) Applicant: Shimadzu Corporation, Kyoto (JP)

(72) Inventor: Shota Sato, Laval (CA)

(73) Assignee: Shimadzu Corporation, Kyoto (JP)

( * ) Notice: Subject to any disclaimer, the term of this patent is extended or adjusted under 35 U.S.C. 154(b) by 679 days.

(21) Appl. No.: 15/922,965

(22) Filed: Mar. 16, 2018

(65) Prior Publication Data
US 2019/0282304 A1    Sep. 19, 2019

(51) Int. Cl.
*A61B 34/20*    (2016.01)
*G06T 11/60*    (2006.01)
(Continued)

(52) U.S. Cl.
CPC ............... *A61B 34/20* (2016.02); *A61B 6/12* (2013.01); *A61B 6/4441* (2013.01); *A61B 6/469* (2013.01); *A61B 6/487* (2013.01); *A61B 6/5235* (2013.01); *A61F 2/95* (2013.01); *G06T 11/60* (2013.01); *A61B 2034/2065* (2016.02); *A61B 2090/376* (2016.02); *A61F 2/82* (2013.01); *A61F 2250/0098* (2013.01); *G06T 2210/41* (2013.01)

(58) Field of Classification Search
CPC ......... A61B 34/20; A61B 6/12; A61B 6/4441; A61B 6/487; A61B 6/469; A61B 6/5235; A61B 2034/2065; A61B 2090/376; A61B 2090/364; A61B 2090/3966; A61B 2090/3764; A61B 6/54; A61B 6/5217; A61B 6/5252; A61B 6/504; G06T 11/60; G06T 2210/41; G06T 11/008; A61F 2/95; A61F 2/82; A61F 2250/0098; G16H 50/30
See application file for complete search history.

(56) References Cited

U.S. PATENT DOCUMENTS

2005/0002546 A1    1/2005  Florent et al.
2010/0256510 A1*  10/2010  Leiblein ................ A61B 90/37
                                                                                600/509
(Continued)

FOREIGN PATENT DOCUMENTS

JP    2005-510288 A    4/2005
JP    2013-215247 A    10/2013

*Primary Examiner* — Hien N Nguyen
(74) *Attorney, Agent, or Firm* — Muir Patent Law, PLLC

(57) ABSTRACT

An X-ray fluoroscopic imaging apparatus which can accurately perform enhancement processing of a device and can also reduce a burden on an operator is provided. An exclusion region E is set so as to surround an obstacle on an X-ray image generated by an image generation unit. A marker extraction unit extracts a marker from a region except for an exclusion region in the X-ray image. An integration unit superimposes a predetermined number of X-ray images on the basis of the position of the marker to generate an integrated image. In this case, detecting obstacle as a marker can be avoided, so the integrated image becomes an image with a stent suitably highlighted. Even in cases where it is difficult to set the region-of-interest so that an obstacle falls out of the range, such as a case in which an obstacle overlaps or is in proximity to a stent, it is easy to set the exclusion region so that the marker is out of range and the obstacle falls within the range. Therefore, the enhancement processing of the stent can be suitably executed according to more various situations.

5 Claims, 16 Drawing Sheets

(51) Int. Cl.
    *A61B 6/12*     (2006.01)
    *A61B 6/00*     (2006.01)
    *A61F 2/95*     (2013.01)
    *A61B 90/00*     (2016.01)
    *A61F 2/82*     (2013.01)

(56)     References Cited

U.S. PATENT DOCUMENTS

| | | | |
|---|---|---|---|
| 2015/0029347 A1* | 1/2015 | Tsubusaki | H04N 5/23219 348/208.1 |
| 2015/0324995 A1* | 11/2015 | Yamamoto | G06K 9/4642 382/173 |

* cited by examiner

X-RAY FLUOROSCOPIC IMAGING APPARATUS

TECHNICAL FIELD

The present invention relates to an X-ray imaging apparatus capable of being effectively used for, e.g., an interventional treatment for capturing an image of a region including a device inserted in a subject's body, and more particularly to a technique for emphasizing a device in an image and displaying the emphasized image.

BACKGROUND ART

In a medical site, a coronary artery interventional treatment (PCI: Percutaneous Coronary Intervention) is performed on patients of myocardial infarction and angina pectoris. In a coronary artery interventional treatment, a catheter equipped with a guide wire and a device therein is inserted into a blood vessel of a subject to perform a treatment of an affected part of a stenosed blood vessel with a device. The position of the catheter inserted in the subject's body is confirmed as needed by continuously capturing an X-ray image.

As a device for use in a coronary artery interventional treatment, a stent for expanding a vascular stenosis portion is used in addition to a roller bladder for cutting the blood vessel wall. A stent is a tubular medical equipment made of metal, etc., and is configured to hold a blood vessel from the lumen by placing it in a strictured segment of an expanded blood vessel using a balloon. Placing a stent in a strictured segment of an expanded blood vessel improves therapeutic effects by a catheter.

In the case of performing a PCI operation using a stent, in order to confirm the position of the stent, an X-ray image is obtained using an X-ray fluoroscopic imaging apparatus. That is, the surgeon irradiates a low dose of an X-ray on a subject and successively acquires an X-ray image showing a catheter or a stent. The operator refers to the continuously displayed real-time X-ray images P and checks the position of the catheter and/or the stent in the blood vessel as needed. Then, as shown in FIG. 15 (a), the catheter 103 is passed through the blood vessel 101 in the direction of the arrow so that the stent 105 reaches the strictured segment 107 which is an affected part.

With reference to the X-ray image P, the surgeon inflates a balloon as shown in FIG. 15 (b) while confirming the positional relationship between the strictured segment 107 and the stent 105 as needed to thereby expand the strictured segment 107 by the expanding stent 105. By pulling out the catheter 103 from the body of the subject through the blood vessel 101, the expanded stent 105 is placed in the blood vessel, so that the blood flow of the affected part is kept normal.

In recent years, in many cases, a plurality of stents is placed in order to further improve the therapeutic effect. In this case, if a gap is formed between stents, there is a possibility that the blood vessel becomes stenosed in between the gaps. For this reason, it is extremely important in an interventional treatment to confirm a position of a stent in a blood vessel.

Conventionally, in order to confirm a position of a stent, an X-ray image is continuously captured using a stent 105 having a material equipped with high radiopaque as a marker 109. The captured X-ray image is displayed on a monitor, and a surgeon refers to the marker appeared on the displayed X-ray image and proceeds with a PCI while confirming the position of the stent as needed.

However, in a PCI, as the position of the stent in the X-ray image periodically moves due to the patient's heartbeat and respiration, it is required for a surgeon to have high skill to perform the positioning of the stent while referring the X-ray image. Further, the stent strut constituting the stent body is lower in radiopaque than the marker, so the contour of the stent strut is low in visibility. Therefore, it is difficult to confirm whether or not the stent strut is normally expanded simply by referring to the marker of the stent.

Under the circumstances, as a technique for improving the visibility of a stent inserted in a body of a subject, a technique of highlighting the stent by using a plurality of continuously captured X-ray images has been proposed (see, for example, Patent Document 1). That is, X-ray images are continuously captured using a stent having a marker, and the captured X-ray images of a plurality of frames are superimposed.

When superimposing, a part having a feature highly related to the marker 109 (for example, a pixel region low in luminance value) is detected as a feature point from each X-ray image. By judging the similarity with the marker for the detected feature point, the position of the actual marker appeared in the X-ray image is specified. By superimposing the X-ray images P of a plurality of frames based on the position of the marker 109 specified by the series of image processing as a reference, an X-ray image (emphasized image) in which the strut of the stent 105 is emphasized can be acquired.

In recent years, as a part of the stent emphasis display technology, a technique in which a region-of-interest is set in an X-ray image has been proposed (see, for example, Patent Document 2). That is, as shown in FIG. 16 (a), a surgeon refers to an X-ray image P displayed on a monitor and sets the region-of-interest R so as to surround the markers 109. In this case, various image processing, such as, e.g., extraction of a feature point and determination of similarity, for specifying the markers 109 is performed on the region-of-interest R in the X-ray image P.

In proceeding with a PCI, in addition to the stent 105 and the markers 109, an object high in radiopaque, such as, e.g., a clip and a pacemaker, that is, an obstacle V, may appear in an X-ray image P in some cases. By setting the region-of-interest R so that the obstacle V falls out of the range in the X-ray image P, it is possible to avoid the situation in which the obstacle V is erroneously recognized as the marker 109.

PRIOR ART

Patent Document

[Patent Document 1]
Japanese Translation of PCT International Application Publication No. JP-T-2005-510288
[Patent Document 2]
Japanese Unexamined Patent Application Publication No. 2013-215247

SUMMARY OF THE INVENTION

Problems to be Solved by the Invention

However, the conventional example having such a configuration has a following problem. That is, in the configuration according to the conventional X-ray fluoroscopic imaging apparatus in which a region-of-interest is set, there is a case in which the position of the marker 109 cannot be specified accurately. As an example, after setting the region-of-interest R, when a surgeon further moves the stent 105 along the blood vessel 101, the position of the marker 109 falls out of the range of the region-of-interest R as shown in FIG. 16 (*b*). In this case, since the position of the marker 109 cannot be specified, the positioning of the stent cannot be performed accurately. Therefore, in order to accurately highlight the stent, it is necessary to re-set the region-of-interest R so as to surround the moved marker 109. As a result, the time required for a PCI increases, resulting in an increased burden of the surgeon.

Further, depending on the positional relationship between the obstacle V and the marker 109, in some cases, it becomes difficult to set the region-of-interest R so as to exclude the obstacle V. As an example, as shown in FIG. 16 (*c*), a case in which the obstacle V is located between the markers 109 or a case in which the obstacle V overlaps with or is in proximity to the stent 105 can be exemplified. In cases where the positional relationship between the obstacle V and the marker 109 is as shown in FIG. 16 (*c*), if the region-of-interest R is set to include each of the markers 109, the obstacle V is included within the range of the region-of-interest R together with the markers 109. Since it is difficult to exclude the obstacle V from the region-of-interest R, the obstacle V is sometimes mistakenly extracted as a marker when performing image processing for identifying the markers 109. As a result, it becomes very difficult to accurately execute the enhancement processing of the stent 105.

The present invention has been made in view of the aforementioned circumstances, and aims to provide an X-ray fluoroscopic imaging apparatus which can accurately perform enhancement processing of a device and can also reduce a burden on an operator.

Means for Solving the Problems

In order to attain such an object, the present invention has the following configuration. That is, an X-ray fluoroscopic imaging apparatus according to the present invention includes an X-ray tube configured to irradiate an X-ray to a subject; an X-ray detector configured to detect the X-ray that transmitted through the subject; an image generation unit configured to generate an X-ray image of a region including a device to be inserted into a body of the subject by using a detection signal output from the X-ray detector; exclusion region setting means configured to set an exclusion region in the X-ray image; marker extraction means configured to extract a marker provided on the device from a range except for the exclusion region in the X-ray image; and an integration unit configured to generate an integrated image by superimposing a plurality of the X-ray images based on a position of the marker extracted by the marker extraction means.

[Functions and Effects] According to the X-ray fluoroscopic imaging apparatus according to the present invention, the exclusion region setting means sets an exclusion region in an X-ray image that the image generation unit generates. The marker extraction unit extracts the marker provided on the device from the range except for the exclusion region in the X-ray image. Based on the position of the marker, the integration unit generates an integrated image by superimposing the plurality of X-ray images.

With such a configuration, even in cases where a radiopaque material, etc., which is likely to be misidentified as a marker, appears in the X-ray image as an obstacle, by setting the exclusion region so as to surround the obstacle, it is possible to assuredly avoid occurrence of misidentifying an obstacle as a marker. For this reason, since the marker extraction means can accurately extract the position of the marker appeared in the X-ray image, it is possible to obtain an integrated image in which the device is more preferably emphasized.

Also, even the case of moving the device during an operation, since the obstacle does not move, it is possible to avoid resetting the exclusion region set once. Therefore, the burden on a surgeon during the PCI can be reduced. Furthermore, even in cases where it is difficult to prevent the situation in which the obstacle overlaps with or is in proximity to the device and therefore the obstacle is misidentified as a marker in a conventional configuration, it is easy to set the exclusion region so that the marker falls out of the range and the obstacle falls within range. Therefore, it is possible to acquire a suitable integrated image according to more various situations and to safely proceed with the operation method of the PCI.

Further, in the aforementioned invention, the X-ray fluoroscopic imaging apparatus preferably further includes an exclusion processed image generation means configured to generate an exclusion processed image by removing the range of the exclusion region from the X-ray image, wherein the marker extraction means extracts the marker from the exclusion processed image.

[Functions and Effects] According to the X-ray fluoroscopic imaging apparatus of the present invention, the exclusion processed image generation means generates an exclusion processed image by removing the range of the exclusion region from the X-ray image. And the marker extraction means extracts the marker from the exclusion processed image. By setting the obstacle which is likely to be misidentified as a marker in the exclusion region, the exclusion processed image becomes an image from which the obstacle is assuredly removed. Since the maker extraction means sets the target from which the marker is extracted as an exclusion processed image, it is possible to assuredly avoid the situation in which the marker extraction means mistakenly extracts the obstacle as a marker. As a result, it is possible to acquire an integrated image in which the device is emphasized suitably and to safely proceed with the PCI operation.

Further, in the aforementioned invention, it is preferable that the marker extraction means detects a candidate of the marker as a feature point from the X-ray image and excludes the feature point included within the range of the exclusion region from the candidate of the marker to extract the marker provided on the device from a range except for the exclusion region in the X-ray image.

[Functions and Effects] According to the X-ray fluoroscopic imaging apparatus of the present invention, the marker extraction means detects a candidate of the marker as a feature point from the X-ray image and excludes the feature point included within the range of the exclusion region from the candidate of the marker to extract the marker from a range excluding the except for the exclusion region in the X-ray image. In such a configuration, by setting the obstacle which is likely to be misidentified as a marker in the exclusion region, even if an obstacle is detected as a feature point, it is assuredly excluded from the candidate of the marker. Therefore, it is possible to assuredly avoid the situation in which the marker extraction means mistakenly extracts an obstacle as a marker.

Further, an obstacle can be excluded from the candidate of the marker by a simple process of selecting a feature point positioned in the range of the exclusion region and releasing the state in which it is detected as the feature point. Therefore, it is possible to simplify the operation required for extracting the marker so as to exclude the obstacle, so that the time required for the marker extraction means to extract the marker can be further shortened.

Further, in the present invention, the X-ray fluoroscopic imaging apparatus preferably further includes obstacle extraction means configured to extract a radiopaque material different from any of the marker and the device as an obstacle from the X-ray image, wherein the exclusion region setting means sets the exclusion region so as to surround the obstacle extracted by the obstacle extraction means.

[Functions and Effects] According to the X-ray fluoroscopic imaging apparatus according to the present invention, the obstacle extraction means extracts a radiopaque material which is different from the marker and the device as an obstacle from the X-ray image. Then, the exclusion region setting means sets the exclusion region so as to surround the obstacle extracted by the obstacle extraction means. In such a configuration, an obstacle is automatically extracted from the X-ray image by the obstacle extraction means. The exclusion region is automatically set at the position surrounding the extracted obstacle by the exclusion region setting means. Thus, the obstacle is automatically excluded from the marker extraction processing by the marker extraction means. Therefore, it is assuredly avoided that the marker extraction means mistakenly extracts an obstacle as a marker, and the process required to exclude the obstacle from the marker extraction processing is shortened. Thus, the burden on the surgeon can be greatly reduced.

Further, in the present invention, the X-ray fluoroscopic imaging apparatus preferably further includes: region-of-interest setting means configured to set a region-of-interest in the X-ray image; and switching setting means configured to switch between a first state in which the exclusion region setting means is in an ON state and a second state in which the region-of-interest setting means is in an ON state, wherein the marker extraction means extracts the marker from the X-ray image excluding the exclusion region in the first state, and extracts the marker from within the range of the region-of-interest in the X-ray image in the second state.

[Functions and Effects] According to the X-ray fluoroscopic imaging apparatus of the present invention, it is provided with the region-of-interest setting means configured to set a region-of-interest in an X-ray image and the switching setting means configured to switch the first state in which the exclusion region setting means is in the ON state and the second state in which the region-of-interest setting means is in the ON state. In the first state, the marker extraction means extracts the marker from the range except for the exclusion region in the X-ray image.

In the second state, the marker is extracted in the range of the region-of-interest in the X-ray image. Since the range of the region-of-interest is generally narrower than the entire range of the X-ray image except for the exclusion region, in the second state, the time required for the marker extraction processing becomes shorter. Therefore, in cases where it is difficult to prevent the situation in which the obstacle overlaps with or is in proximity to the device and therefore the obstacle is misidentified as a marker in a conventional configuration, it is possible to assuredly exclude the obstacle as a first state from the target of the marker extraction processing. In cases where the obstacle is away from the device, as a second state, the marker extraction processing can be performed in a shorter time. In this way, depending on the situation of PCI, it is possible to acquire an accumulated image in which the device is subjected to the enhancement processing under more favorable conditions.

Effects of the Invention

According to the X-ray fluoroscopic imaging apparatus according to the present invention, the exclusion region setting means sets an exclusion region in an X-ray image that the image generation unit generates. The marker extraction unit extracts the marker provided on the device from the range except for the exclusion region in the X-ray image. Based on the position of the marker, the integration unit generates an integrated image by superimposing the plurality of X-ray images.

With such a configuration, even in cases where a radiopaque material, which is different from either the marker or the device, appears in the X-ray image as an obstacle, by setting the exclusion region so as to surround the obstacle, it is possible to assuredly avoid occurrence of misidentifying an obstacle as a marker 51. For this reason, since the marker extraction means can accurately extract the position of the marker appearing in the X-ray image, it is possible to obtain an integrated image in which the device is more preferably emphasized.

Further, even in the case of moving the device during the operation, since the obstacle does not move, it is possible to avoid resetting the exclusion region set one. Therefore, the burden on a surgeon during the PCI can be reduced. Furthermore, even in cases where it is difficult to prevent the erroneous detection between the obstacle and the marker by a conventional configuration, it is easy to set the exclusion region so that the marker falls out of the range and the obstacle falls within range. Therefore, it is possible to acquire a suitable integrated image according to more various situations and to safely proceed with the operation of the PCI.

EMBODIMENTS FOR CARRYING OUT THE INVENTION

Example 1

Figure 1:
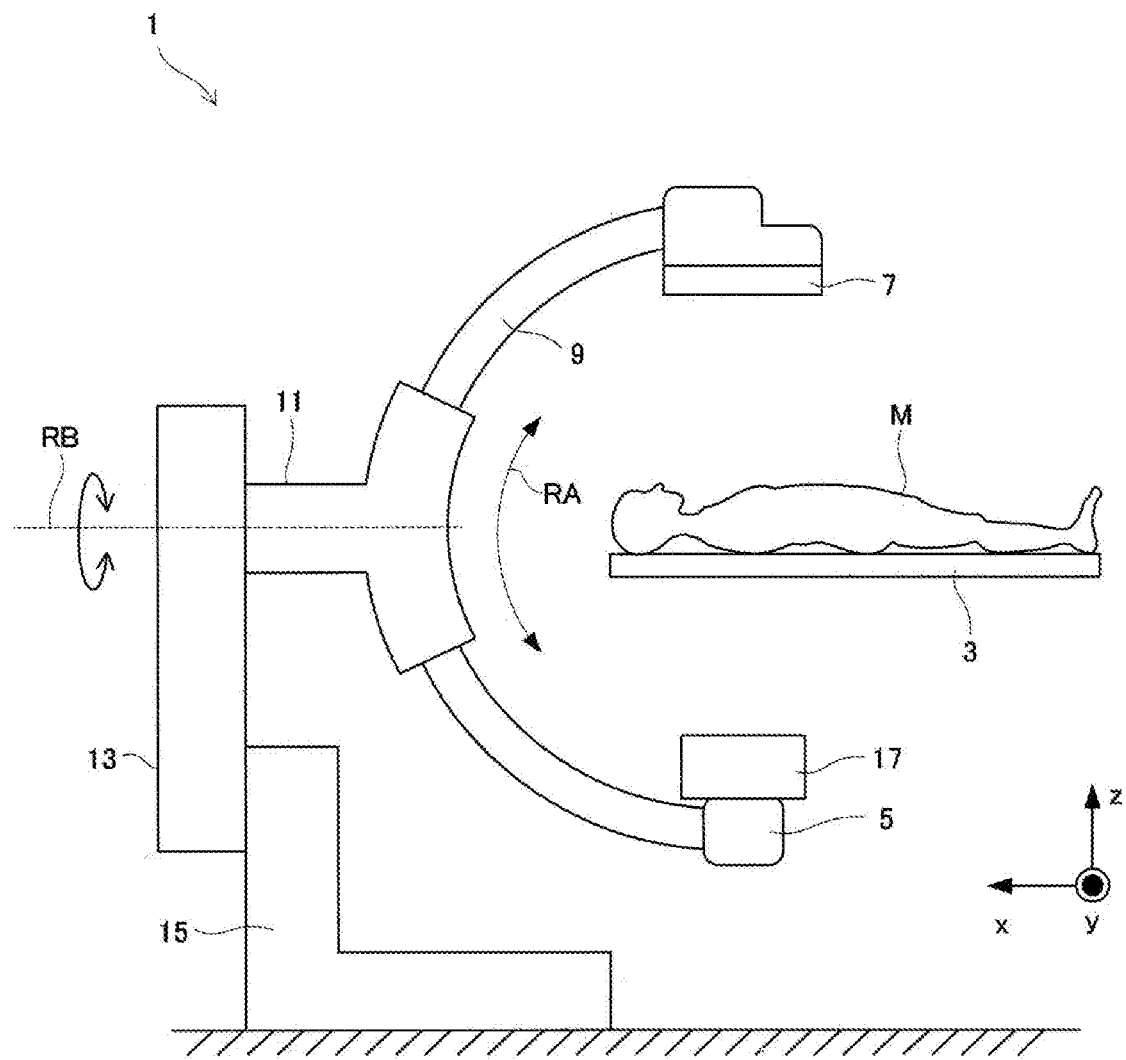
FIG. 1 is a schematic diagram illustrating an overall configuration of an X-ray fluoroscopic imaging apparatus according to Example 1.
Figure 2:
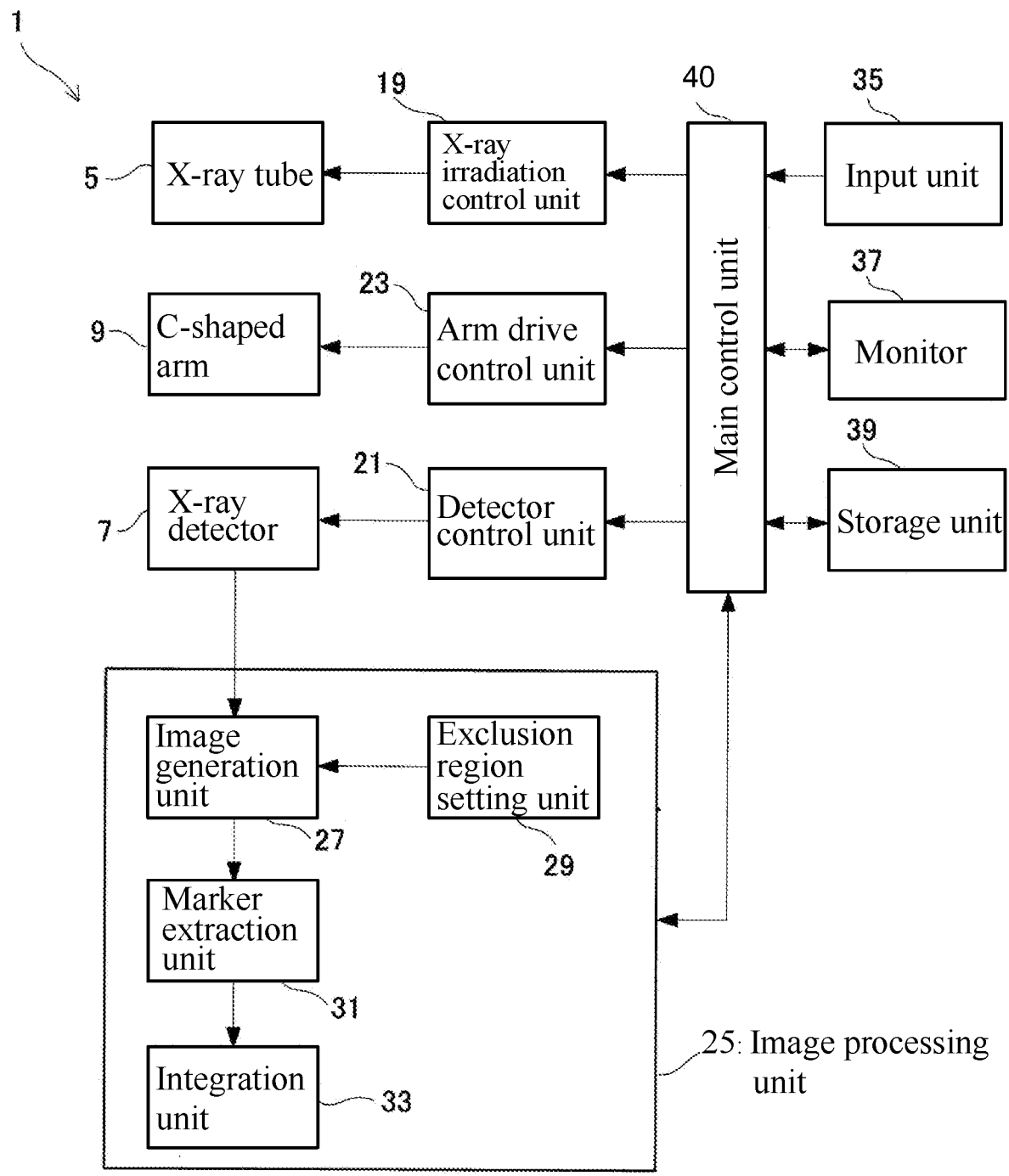
FIG. 2 is a functional block diagram illustrating the configuration of the X-ray fluoroscopic imaging apparatus according to Example 1.

Hereinafter, Example 1 of the present invention will be described with reference to the drawings. FIG. 1 is a front view illustrating a configuration of an X-ray fluoroscopic imaging apparatus according to Example 1, and FIG. 2 is a functional block diagram illustrating a configuration of an X-ray fluoroscopic imaging apparatus according to Example 1.

<Description of Overall Configuration>

An X-ray fluoroscopic imaging apparatus 1 according to Example 1 is provided with a top board 3 on which a subject M is placed, an X-ray tube 5 that irradiates an X-ray to the subject M, and an X-ray detector 7 configured to detect the X-ray irradiated from the X-ray tube 5 and convert it into a charge signal. The X-ray tube 5 and the X-ray detector 7 are arranged so as to oppose to each other across the top board 3. The X-ray detector 7 is equipped with a detection surface for detecting an X-ray, and X-ray detection elements are two-dimensionally arranged on the detection surface. In Example, it is assumed that a flat panel type detector (FPD) is used as the X-ray detector 7.

The X-ray tube 5 and the X-ray detector 7 are provided at one end of the C-shaped arm 9 and the other end thereof, respectively. The C-shaped arm 9 is held by an arm holding member 11 and configured to slide along the circular arc path of the C-shaped arm 9 indicated by the reference symbol "RA". The arm holding member 11 is arranged on the side surface of the support 13 and is configured to be rotatable about the axis of the horizontal axis RB parallel to the x-direction (the longitudinal direction of the top board 3 and the body axis direction of the subject M). The C-shaped arm 9 held by the arm holding member 11 rotates about the axis of the x-direction in accordance with the arm holding member 11.

The support 13 is supported by a support base 15 disposed on the floor surface, and is configured so as to be horizontally movable in the y-direction (in the short direction of the top board 3). The arm supporting member 11 and the C-shaped arm 9 supported by the support 13 move in the y-direction in accordance with the horizontal movement of the support 13. The collimator 17 is mounted on the X-ray tube 5 and limits the X-ray irradiated from the X-ray tube 5 to a cone shape which is a pyramid.

Here, the configuration of the X-ray imaging apparatus 1 will be described in more detail. As shown in FIG. 2, the X-ray imaging apparatus 1 is provided with an X-ray irradiation control unit 19, a detector control unit 21, an arm drive control unit 23, and an image processing unit 25. The X-ray irradiation control unit 19 is configured to output a high voltage to the X-ray tube 5. Based on the high voltage output given by the X-ray irradiation control unit 19, the X-ray dose that the X-ray tube 5 irradiates and the timing for irradiating an X-ray are controlled. The detector control unit 21 controls the operation of reading the charge signal converted by the X-ray detector 7, that is, the X-ray detection signal.

The arm drive control unit 23 controls the sliding movement of the C-shaped arm 9. As the C-shaped arm 9 slides in the direction indicated by the symbol "RA", the spatial position of each of the X-ray tube 5 and the X-ray detector 7 changes while maintaining the opposed arrangement state. The arm drive control unit 23 totally controls the rotational movement of the arm supporting member 11 in addition to the sliding movement of the C-shaped arm 9. Since the X-ray tube 5 and the X-ray detector 7 are mounted on the C-shaped arm 9, each spatial position changes while maintaining the opposed arrangement state in accordance with the rotational movement of the arm supporting member 11.

The image processing unit 25 is provided with an image generation unit 27, an exclusion region setting unit 29, a marker extraction unit 31, and an integration unit 33. The image generation unit 27 is provided at the subsequent stage of the X-ray detector 7, and intermittently generates an X-ray image based on the X-ray detection signal output from the X-ray detector 7.

The exclusion region setting unit 29 is connected to the image generation unit 27, and sets an exclusion region in the X-ray image generated by the image generation unit 27 according to the instruction content input to the input unit 35 which will be described later. The marker extraction unit 31 is provided at the subsequent stage of the exclusion region setting unit 29. The marker extraction unit 31 extracts each of the markers 51, which will be described later, from the range except for the exclusion region in the X-ray image generated by the image generation unit 27. The exclusion region setting unit 29 corresponds to the exclusion region setting means in the present invention.

As the outline of extracting the marker 51 by the marker extraction unit 31, the X-ray image is scanned and a portion low in luminance value is detected as a feature point (a point which becomes a candidate of the marker 51). Then, by determining the similarity with the predetermined marker among the detected feature points, the position of the actual marker 51 appeared in the X-ray image is extracted. Details of the process of extracting the marker 51, such as, e.g., a detection of a feature point and similarity determination, are described in detail in Patent Document 1 and Reference Document 1 (Reference Document 1: Japanese Patent No. 5,523,791) and so forth, so the description will be omitted here. Note that the marker extraction unit 31 corresponds to the marker extraction means and the exclusion processed image generation means in the present invention.

The integration unit 33 is provided at the subsequent stage of the marker extraction unit 31. The integration unit 33 superimposes the X-ray images generated by the image generation unit 27 based on the marker extracted by the marker extraction unit 31 to generate an integrated image.

The X-ray imaging apparatus 1 is further provided with an input unit 35, a monitor 37, a storage unit 39, and a main control unit 40. The input unit 35 is for inputting an operator's instruction, and as an example thereof, a panel of a keyboard input type, a mouse input type, or a touch input type can be exemplified.

The monitor 37 displays various images, such as, e.g., an X-ray image generated by the image generation unit 27 and an integrated image generated by the integration unit 33. The exclusion region set by the exclusion region setting unit 29 is superimposed and displayed on the X-ray image by the monitor 37. The storage unit 39 stores the information on the exclusion region set by the exclusion region setting unit 29, and the like, in addition to the X-ray image generated by the image generation unit 27, etc., and the integrated image generated by the integration unit 33. The main control unit 40 totally controls each of the X-ray irradiation control unit 19, the detector control unit 21, the arm drive control unit 23, the image processing unit 25, the monitor 37, and the storage unit 39.

Figure 3:
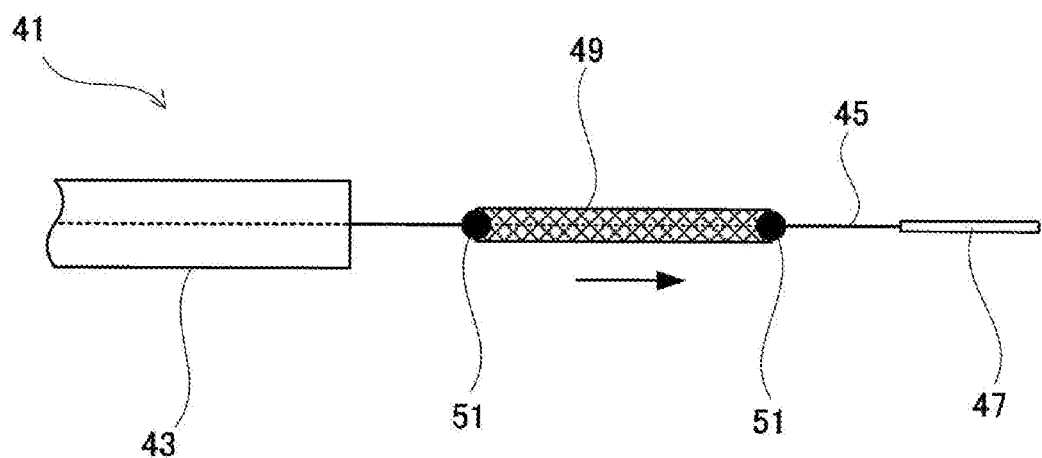
FIG. 3 is a schematic diagram illustrating a configuration of a catheter according to Example 1.

FIG. 3 is a schematic diagram showing the configuration of a catheter system 41 for use in an interventional treatment. The catheter system 41 is equipped with a catheter 43, a wire 45, a guide wire 47, and a stent 49. The wire 45 is inserted in the tubular catheter 43. At the tip of the wire 45, the guide wire 47 is provided. The stent 49 is provided on the wire 45 connecting the catheter 43 and the guide wire 47.

The stent 49 is formed into a cylindrical shape with a mesh of a metal wire such as stainless steel, and a balloon (not shown) is provided therein. The stent 49 is configured to be movable along the wire 45. Further, the stent 49 is provided with markers 51. In Example 1, the number of markers 51 is two, but the number of markers 51 may be changed as required. Of the two markers 51, one of the markers 51 is provided on the tip side of the stent 49, and the other of the markers 51 is provided on the base end side of the stent 49.

In an interventional treatment, the stent 49 is arranged at a stenosed portion of a blood vessel. Then, the stent 49 arranged as described above is inflated with a balloon, and the expanded stent 49 is placed in the blood vessel, so that the stenosed blood vessel is expanded to keep the blood flow normal. Each of the markers 51 is constituted by a radiopaque material, and specifies the position of the stent 49 in the X-ray image. As an example of the material constituting the marker 51, a metal, such as, e.g., gold, platinum, and tantalum, can be exemplified. Note that the stent 49 corresponds to a device in the present invention.

<Description of Operation>

Figure 4:
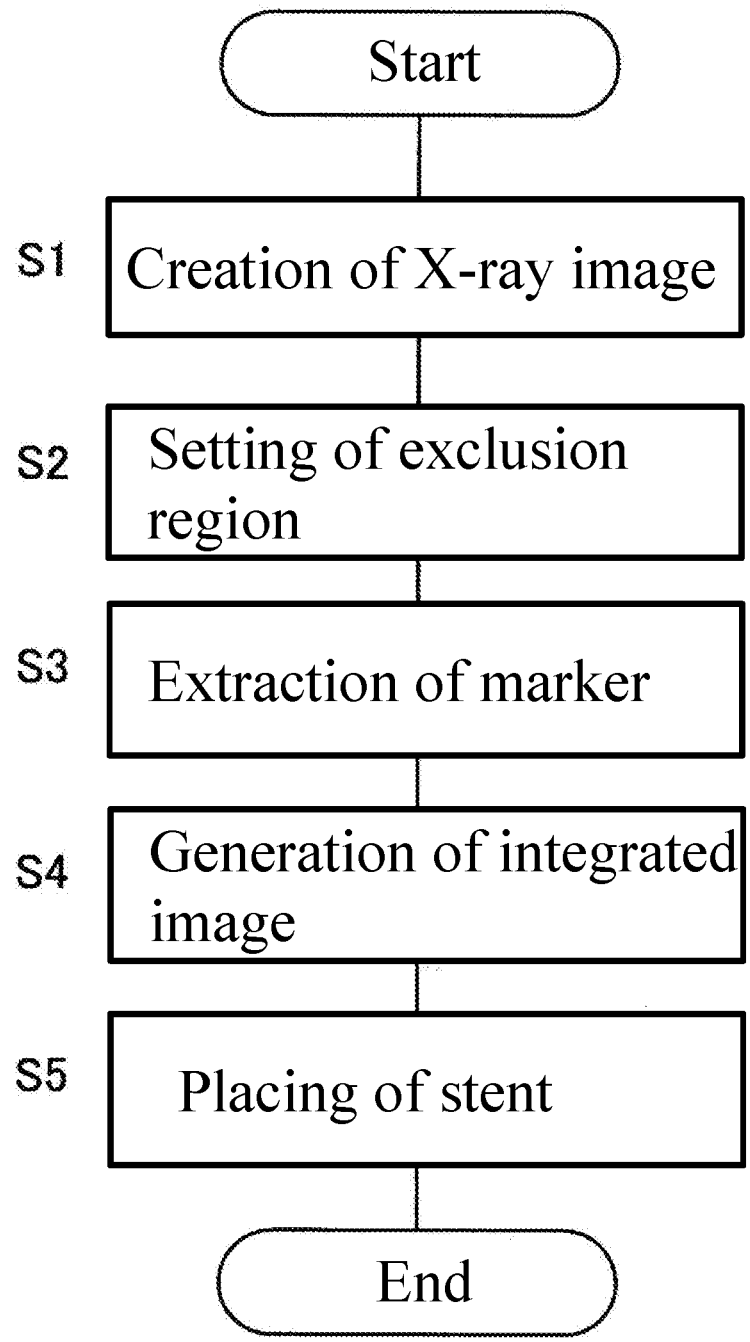
FIG. 4 is a flowchart explaining steps of an operation according to the X-ray fluoroscopic imaging apparatus according to Example 1.

Next, the operation of the X-ray fluoroscopic imaging apparatus 1 according to the example will be described. In performing the explanation, a process of performing an interventional treatment using the X-ray fluoroscopic imaging apparatus 1 will be used as an example. FIG. 4 is a flowchart describing the operation steps of the X-ray fluoroscopic imaging apparatus 1 according to Example 1.

Step S1 (X-ray Image Capturing)

In performing an interventional treatment, a surgeon first makes a small hole in the brachial artery or the femoral artery of the subject M and inserts the catheter 43 into the blood vessel. After inserting the catheter 43 into the blood vessel of the subject M, X-ray image capturing is performed sequentially. That is, the X-ray is intermittently irradiated to the subject M from the X-ray tube 5. The X-ray that has passed through the subject M is detected by the X-ray detector 7.

The detected X-ray is converted into an X-ray detection signal which is an electric signal, and the converted X-ray detection signal is output to the image generation unit 27. Based on the output X-ray detection signal, the image generation unit 27 intermittently generates an X-ray image P in which the catheter 43, the stent 49, etc., appear. In Example 1, the capturing of the X-ray image P is performed at a frame rate of, e.g., about 15 to 30 FPS. The real time X-ray image P generated by the image generation unit 27 is continuously displayed on the monitor 37.

Figure 5:
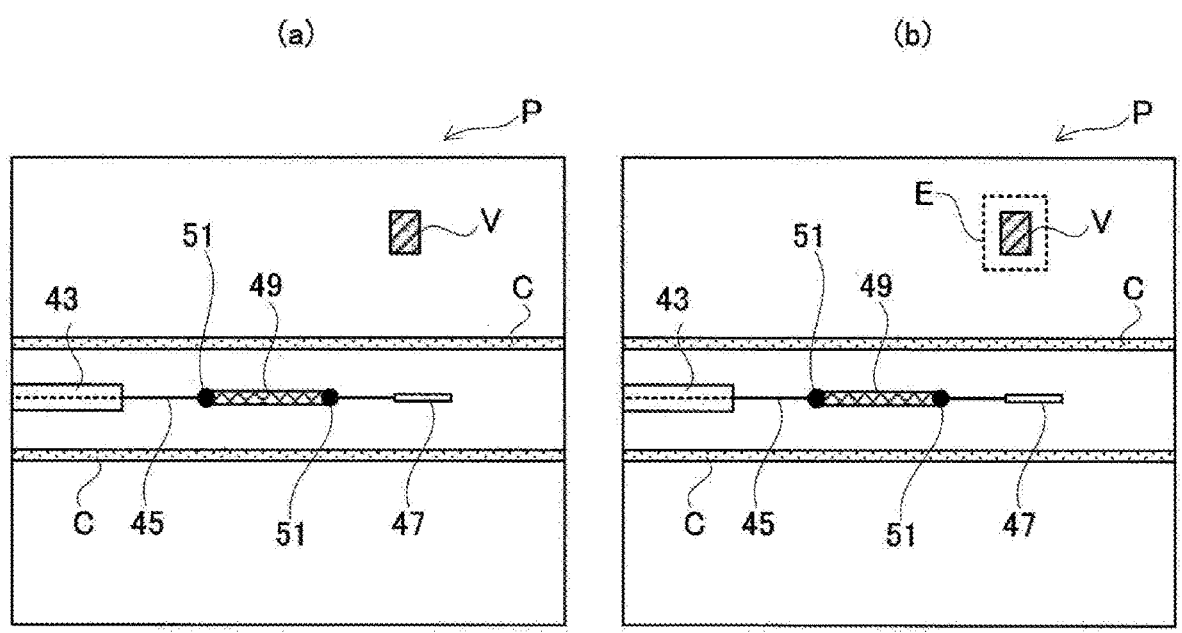
FIG. 5 is a diagram showing an X-ray image generated in Example 1. (a) is an X-ray image before setting an exclusion region, and (b) is an X-ray image in a state in which the exclusion region is set.

FIG. 5 (*a*) is a diagram showing an example of an X-ray image P displayed on the monitor 37. The X-ray image P shows a state in which the catheter 43 is inserted into the blood vessel C and the stent 49 is advanced along the wire 45.

Step S2 (Setting of Exclusion Region)

As will be described later, the X-ray fluoroscopic imaging apparatus 1 has a configuration in which image processing for extracting the marker 51 provided on the stent 49 from the X-ray image P is performed and a plurality of X-ray images P is superimposed based on the marker 51 as a reference. However, there are cases in which a pacemaker and/or a clip is placed in the vicinity of a heart of a subject M due to the past medical treatment. Pacemakers and clips are made of a material high in radiopaque, such as, e.g., metal, in the same manner as in the marker 51. For this reason, as shown in FIG. 5 (*a*), when a radiopaque material (obstacle V) which is neither the markers 51 nor the stent 49, such as a pacemaker, appears in the X-ray image P, there is a possibility that the obstacle V is erroneously extracted at the time of performing the image processing for extracting the markers 51.

Therefore, as a characteristic feature of the present invention, a surgeon sets the exclusion region, i.e., a region from which the target of extracting the marker 51 is excluded. That is, a surgeon views the real-time X-ray image P displayed on the monitor 37 and specifies the position and the range of the exclusion region E so as to surround the obstacle V (see FIG. 5 (*b*)). Specifying the exclusion region E is performed by operating the input unit 35, etc. As an example of the specifying method, a method in which setting is performed by operating a cursor by a mouse input, a method in which a boundary line of the exclusion region E is directly depicted on the monitor 37 using a touch pen, etc., can be exemplified.

The exclusion region setting unit 29 sets the exclusion region E to the X-ray image P according to the content of the instruction that a surgeon inputs to the input unit 35. It is preferable to set the range of the exclusion region E so that the obstacle V fall always within the range of the exclusion region E, taking into consideration of the range of the periodic movements due to the body movements of the subject M. The information of the set exclusion region E is stored in the storage unit 39 and superimposed and displayed on the X-ray image P on the monitor 37. The information on the position of the exclusion region E and the range thereof is transmitted to the marker extraction unit 31 together with each information of the X-ray image P.

Step S3 (Extraction of Marker)

Figure 6:
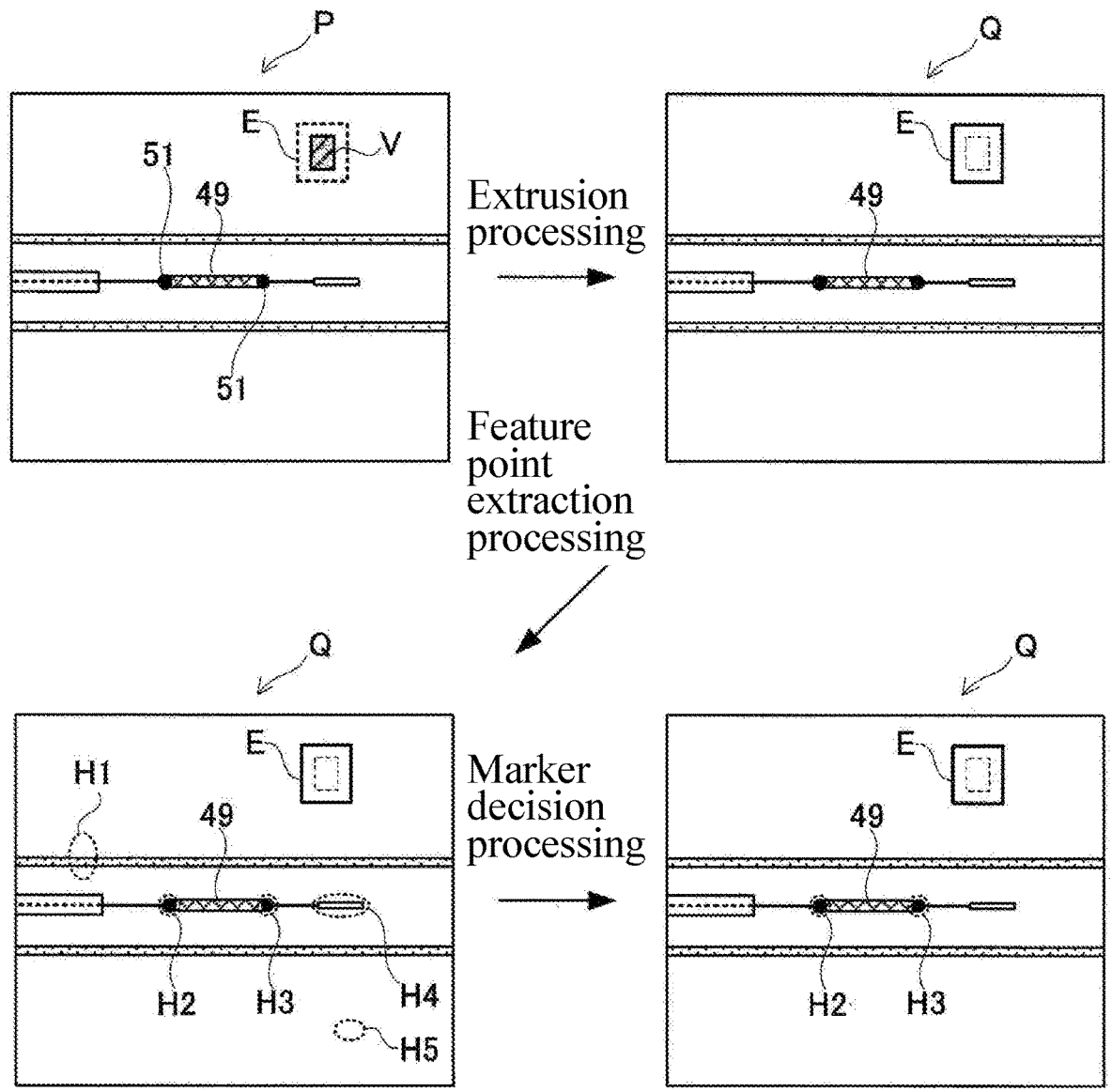
FIG. 6 is a diagram explaining various kinds of image processing to be executed in Step S3 of Example 1.

After setting the exclusion region, image processing for extracting the marker is performed with respect to the X-ray image. The marker extraction unit 31 performs image processing (exclusion processing) for excluding the exclusion region E from the X-ray image P (see FIG. 6, upper left figure) to generate the exclusion processed image Q (FIG. 6, upper right figure). Then, feature point detection processing is executed with respect to the exclusion processed image Q. By the feature point detection processing, pixel regions small in luminance value in the exclusion processed image Q are detected as feature points H. It is assumed that feature points H detected in Example 1 are regions indicated by the reference symbols H1 to H5 (see FIG. 6, lower left figure). Since the marker 51 is a material high in radiopaque, the region where the actual marker 51 appears is small in luminance value. Therefore, the region where the marker 51 appears is assuredly detected as a feature point H.

Then, marker determination processing is performed on each of the feature points H, so that the actual marker 51 is specified from the feature points H. Various reference parameters which become the criteria of the marker 51 are stored in advance in the storage unit 39, and the marker extraction unit 31 extracts accurate position information of the marker 51 from the X-ray image P by specifying the marker 51 from the feature points H based on the reference parameter. In Example 1, the feature points H2 and H3 among feature points H1 to H5 are determined as actual markers 51 (FIG. 6, lower right figure).

In a configuration in which the exclusion region is not set like a prior art, the feature point detection processing is performed on the entire X-ray image P. In this case, the obstacle V appeared in the X-ray image P is also detected as a feature point R. On the other hand, in Example 1, since the region in which the obstacle V appears is set as the exclusion region E, the obstacle V is not included in the exclusion processed image Q. Therefore, since the obstacle V is not detected as a feature point in Step S3, extraction of the obstacle V as a marker can be assuredly avoided. Each of the X-ray images P from which the position of the marker 51 is extracted is transmitted to the integration unit 33.

Step S4 (Generation of Integrated Image)

Figure 7:
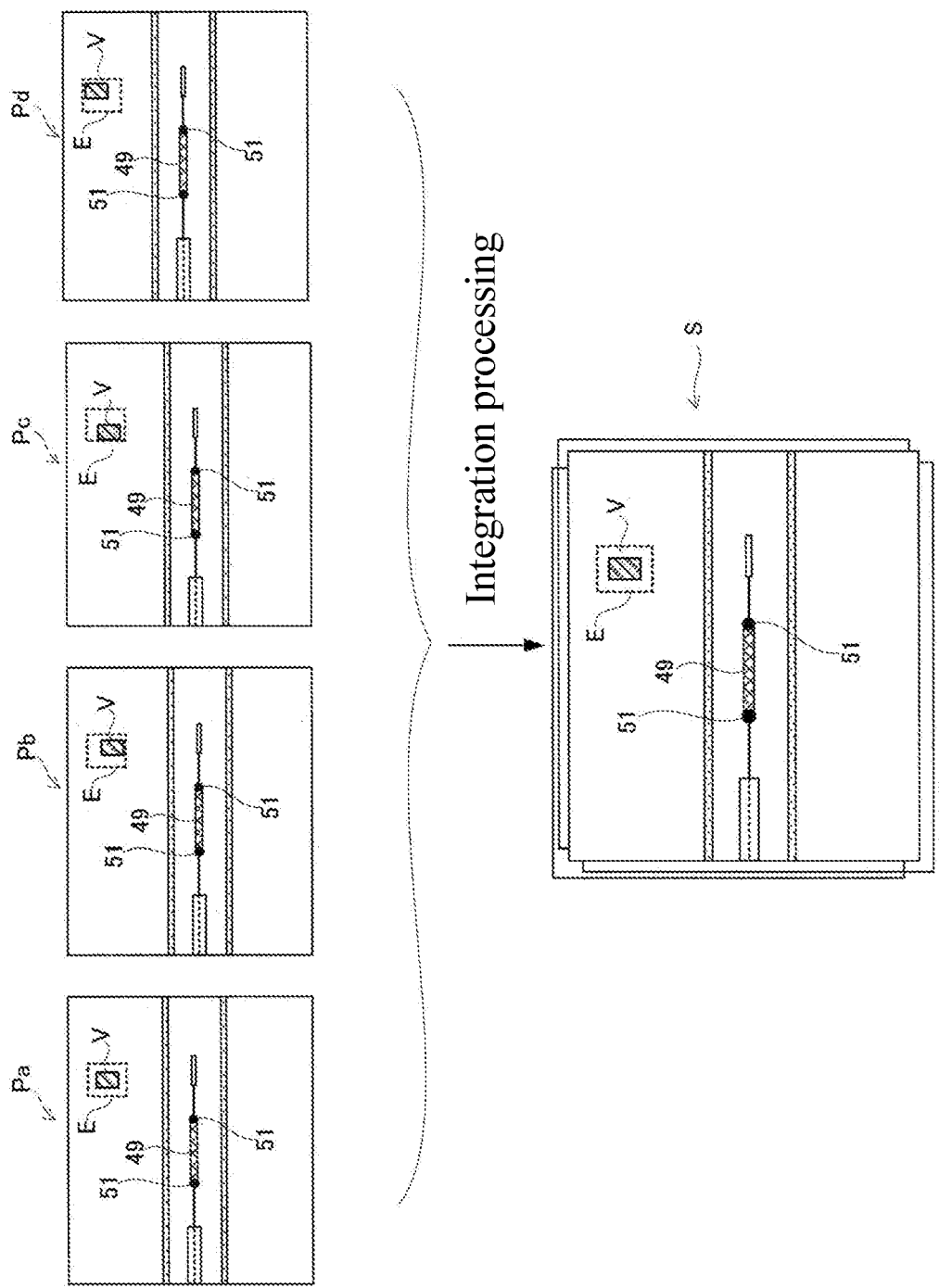
FIG. 7 is a diagram illustrating integration processing executed in Step S4 of Example 1.

After the marker extraction processing is performed with respect to the X-ray image P, generation of an integrated image is performed. That is, the integration unit 33 performs integration processing to highlight the real-time image of the stent 49. The integration processing is image processing for generating an integrated image by superimposing a predetermined number of most recently acquired X-ray images P. In Example 1, the number of X-ray images P used for the superimposing processing is four, but the number of images may be changed as appropriate. Note that the number of X-ray images P used for the superimposing processing is preferably the number of X-ray images P generated in the period of one heartbeat of the subject M. It is assumed that the latest X-ray image P generated most recently by the image generation unit 27 is the X-ray image Pa and X-ray images P new next to the X-ray image Pa are denoted by the symbols Pb to Pd in order (see FIG. 7, upper row).

The integration unit 33 selects the four most recently generated X-ray images Pa to Pd out of a series of X-ray images P in which the marker extraction processing was performed. Due to the pulse of the subject and the respiration thereof, the positions of the stent 49 appeared in each of the X-ray images Pa to Pd are different from each other. Therefore, the integration unit 33 performs position adjustment processing of the X-ray images Pa to Pd with each marker 51 as a reference. Then, the integration unit 33 superimposes the X-ray images Pa to Pd to which the position adjustment processing was executed to generate an integrated image S (see FIG. 7, lower row). The acquired integrated image S is displayed on the monitor 37.

After completion of the step of Step S4, the steps of Steps S2 to S4 are further repeated. By repeating the steps of Steps S2 to S4, the real-time image of the stent 49 high in visibility is intermittently displayed as an integrated image S. Therefore, a surgeon can safely proceed with the operation of the PCI by confirming the integrated image S and advance the catheter 43 to the target coronary artery.

Step S5 (Placing of Stent)

A surgeon performs placing of the stent while referring to the integrated image S which is displayed intermittently on the monitor 37. That is, a surgeon causes the catheter 43 to reach the strictured segment of the coronary artery while confirming the X-ray image of the stent 49 appeared in the integrated image S. And the surgeon inflates a balloon provided in the stent 49. Since the stent 49 is expanded by the balloon, the narrowed coronary artery is expanded. The blood flow of the coronary artery is kept normal by placing the expanded stent 49 in the blood vessel. After placing the stent 49, the catheter 43 is pulled out of the subject M through the blood vessel C, and the PCI is terminated.

In Step S4, position adjustment processing is performed with the marker 51 as a reference, so that the positions of the stent 49 appearing on each of the X-ray images Pa to Pd are the same. Therefore, as a result of superimposing the X-ray images Pa to Pd, the stent 49 appearing on the integrated image S becomes an enhanced image. Therefore, in the integrated image S, since the visibility of the strut and the contour of the stent 49 is enhanced, a surgeon can easily and assuredly confirm that the stent 49 is normally expanded. Also, since the visibility of the stent 49 is high, a surgeon can more precisely adjust the positional relationship between the stent 49 already placed and the stent 49 to be newly placed. As a result, it is possible to more assuredly prevent the blood vessel from becoming stenosed again after execution of the PCI.

Effects by Configuration of Example 1

The X-ray fluoroscopic imaging apparatus 1 according to Example 1 has a configuration in which an exclusion region is set in an X-ray image. The marker extraction unit 31 performs extraction processing of the marker 51 using an X-ray image except for the exclusion region, and the integration unit 33 performs integration processing based on the position information of the extracted marker 51. By setting the exclusion region so as to enclose an obstacle V which is likely to be misrecognized as a marker 51, such as, e.g., a pacemaker and a clip, the obstacle V is excluded from the target of the marker extraction processing. In other words, it is avoided that the obstacle V is erroneously extracted as the marker 51, so that the positioning of each X-ray image can be performed more accurately in the integration processing by the integration unit 33. Therefore, the visibility of the stent 49 in the integrated image S can be improved.

Here, compared with a conventional configuration in which a region-of-interest is set and the range within the range of-interest is targeted for marker extraction processing as shown in Patent Document 2, the effect of the configuration for setting the exclusion region according to Example 1 will be described in more detail.

When performing the PCI, it is necessary to strictly adjust the position of the stent in order to avoid occurrence of restenosis. For this reason, a surgeon moves the position of the stent frequently along the blood vessel. Therefore, in the conventional configuration in which the region-of-interest R is set, the surgeon further moves the stent 105 after setting the region-of-interest R. As a result, a situation in which the position of the marker 109 falls outside the region-of-interest R (FIG. 16 (a) and FIG. 16 (b)) occurs frequently.

In this case, it is not possible to specify the position of the marker 109 as a reference for position alignment. Therefore, when performing the integration processing, it is difficult to accurately align each of the stents 105 appeared on a plurality of X-ray images. Therefore, in order to accurately highlight the alignment of the stents 105, it is necessary to re-set the region-of-interest R so as to surround the moved stent 105. As a result of frequently re-setting the region-of-interest R, the time required for the PCI increases, resulting in an increased burden of the surgeon.

Figure 8:
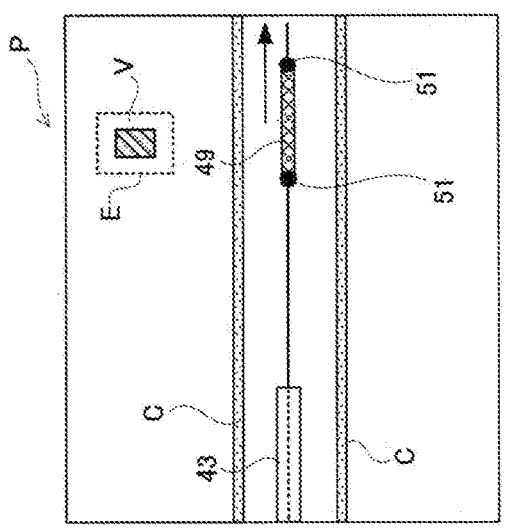
FIG. 8 is a diagram illustrating effects of a configuration of Example 1. (a) is an X-ray image before moving a stent, (b) is an X-ray image after moving the stent, (c) is an X-ray image showing a state in which an obstacle and the stent are overlapped and the setting of the region-of-interest is difficult.
Figure 8:
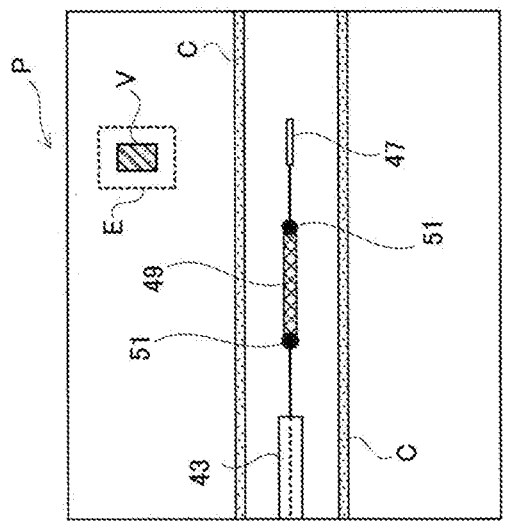
Figure 8:
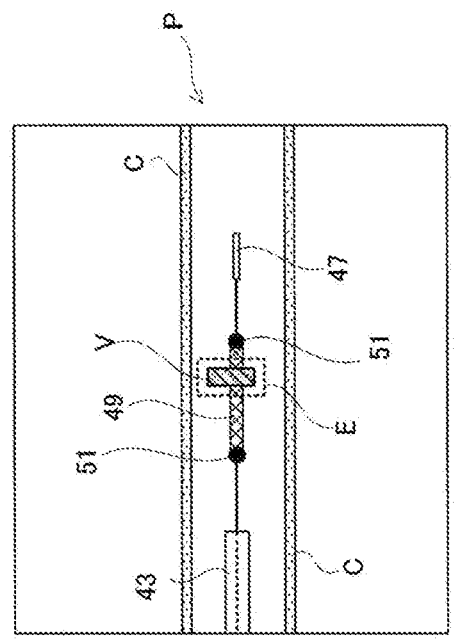

On the other hand, in the X-ray fluoroscopic imaging apparatus 1 according to Example 1, an exclusion region E is set so as to surround the obstacle V that may be erroneously recognized as a marker 51 (FIG. 8 (a)). In the PCI, the obstacle V is not a target of the move operation for a surgeon. Therefore, unlike the stent 49, the obstacle V does not move significantly during the PCI. Therefore, even when a surgeon moves the stent 49, the obstacle V is located within the range of the exclusion region E (FIG. 8 (b)). Therefore, since the situation in which the exclusion region E is re-set can be assuredly avoided, the enhancement processing of the stent 49 can be executed more favorably and the burden of surgeon can be reduced.

Figure 16:
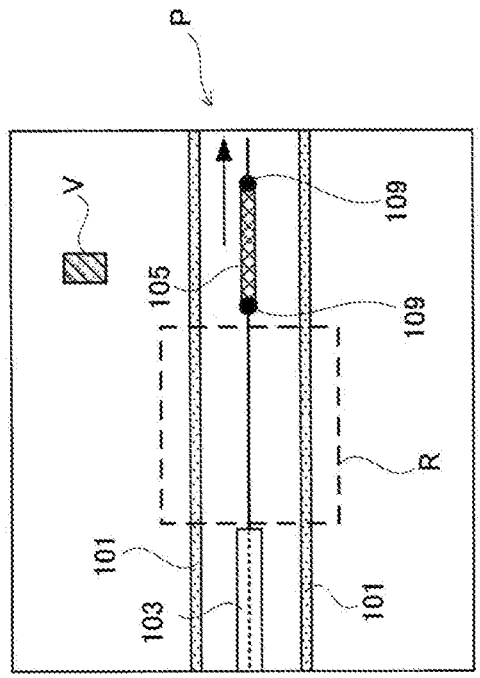
FIG. 16 is a schematic diagram for explaining a problem of a conventional example. (a) is an X-ray image before moving a stent, (b) is an X-ray image after moving the stent, and (c) is an X-ray image showing a state in which an obstacle and the stent are overlapped and the setting of the region-of-interest is difficult.
Figure 16:
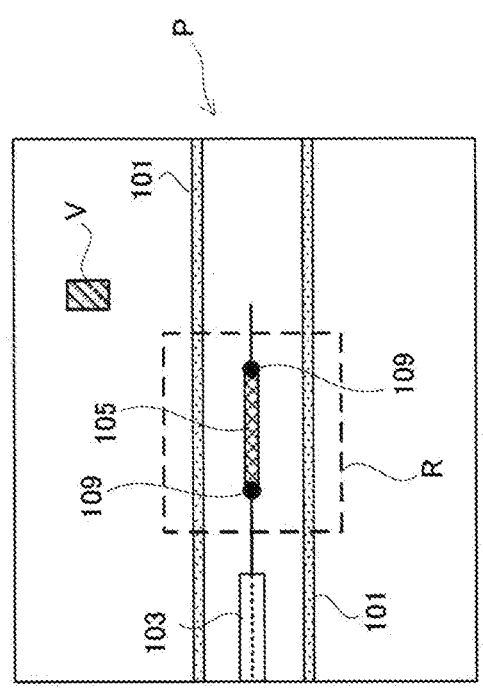
Figure 16:
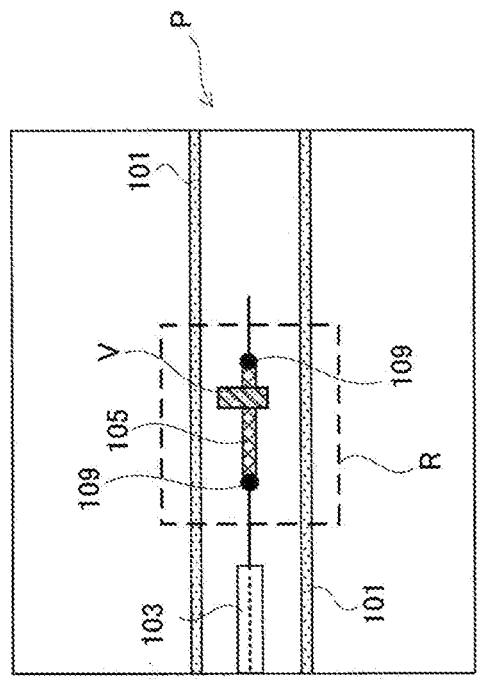

Also, in a conventional configuration in which the region-of-interest R is set, as shown in FIG. 16 (b), depending on the positional relationship between the obstacle V and the marker 109, it becomes difficult to set the region-of-interest R so as to exclude the obstacle V. However, in Example 1, the exclusion region can be appropriately set in an arbitrary range including the obstacle V. Therefore, even in cases where the obstacle V and the stent 105 are in a positional relationship in which they are overlapped (or closely arranged) as shown in FIG. 16 (b), the exclusion region E can be easily set so that the marker 51 becomes out of the range and the obstacle V becomes within the range (FIG. 8 (c)). Therefore, since the obstacle V can be assuredly excluded at the time of the marker extraction processing, it is possible to accurately specify the position of the marker 51 in the X-ray image P according to more various situations, more preferably acquire the integrated image S with the stent 49 emphasized.

Further, the X-ray fluoroscopic imaging apparatus 1 according to Example 1 can obtain a more advantageous effect in cases where an interventional treatment is performed on a region where a blood vessel branches, as compared with the conventional configuration. Such effects will be described with reference to the drawings.

Figure 9:
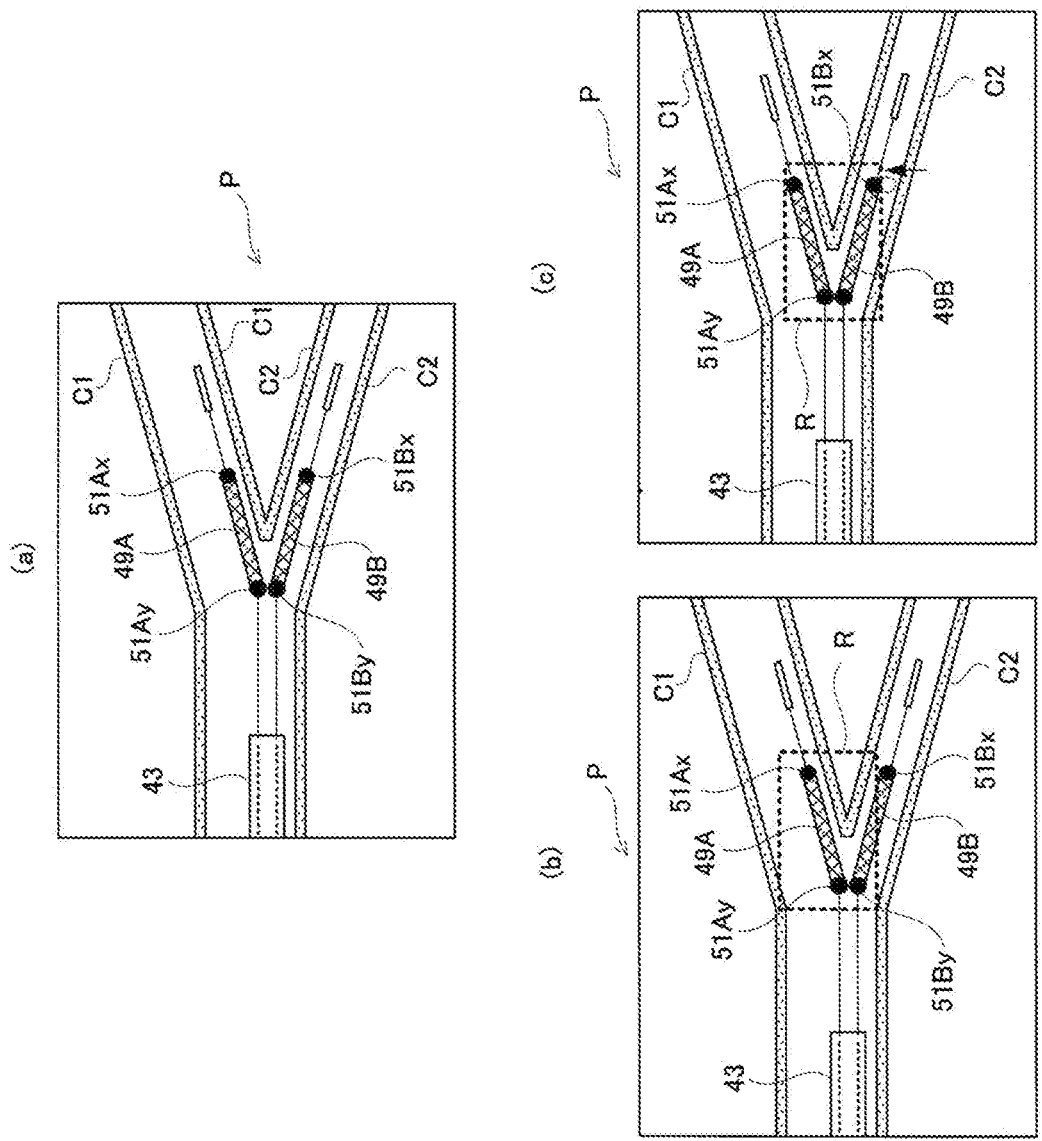
FIG. 9 is a diagram illustrating effects of the configuration of Example 1 in a PCI for branched blood vessels. (a) is an X-ray image showing a state of performing a PCI by the Kissing method, (b) is an X-ray image in a state in which the region-of-interest is set in a conventional example, and (c) is an X-ray image showing a state in which the marker is displaced by a body movement after setting the region-of-interest in the conventional example.

In recent years, there is a strong demand for performing a treatment of complicated structural parts, such as branched blood vessels, by a Kissing method, etc. When a PCI is performed on the branch portion of the blood vessel by the Kissing method, as shown in FIG. 9 (a), the first stent 49A is placed along the trunk blood vessel C1 and the second stent 49B is placed along the branched blood vessel C2. In this case, the enhancement processing is performed on one of two stents 49. That is, when a surgeon is manipulating the stent 49A, the enhancement processing is performed on the stent 49A.

Note that markers 51 are distinguished such that a maker 51 to be provided on the stent 49A is denoted as a marker 51A and a marker 51 to be provided on the stent 49B is denoted as a marker 51B. Further, the marker 51A to be provided on the distal end side of the stent 49A is denoted as a marker 51Ax, and the marker 51A to be provided on the proximal end side of the stent 49A is denoted as a marker 51Ay. Further, the marker 51B to be provided on the distal end side of the stent 49B is denoted as a marker 51Bx, and the marker 51B to be provided on the proximal end side of the stent 49B is denoted as a marker 51By.

In cases where enhancement processing of the stent 49A is performed in a conventional configuration for setting the region-of-interest, it is ideal to set the region-of-interest R so as to surround the marker 51Ax and the marker 51Ay. In cases where marker extraction processing is performed after setting the region-of-interest R, the marker extraction processing is performed by searching only within the region-of-interest R of the X-ray image P, so the marker 51Ax and the marker 51Ay are extracted.

Here, the images, such as, e.g., the blood vessel, the markers 51, and the stent 49 appeared on the X-ray image P, are periodically displaced due to the body movements by the heartbeat and the respiration of the subject M. For this reason, the boundary line of the region-of-interest R is set slightly wider so that each marker 51A falls within the range of the region-of-interest R through the period of the body movement (FIG. 9 (b)). Depending on the angle between the trunk blood vessel C1 and the branched blood vessel C2, the position of the marker 51Bx is close to the boundary of the region-of-interest R. In that case, the marker 51Bx may sometimes be included within the range of the region-of-interest R due to the minute movements of the position of the marker 51Bx due to the body movements by the heartbeat and the respiration of the subject M (FIG. 9 (c)).

When the marker 51Bx is included within the range of the region-of-interest R, the marker 51Bx is extracted in addition to each of markers 51A from the region-of-interest R by the marker extraction processing. Since the position of the marker 51A and the position of the marker 51Bx are clearly different from each other, the marker 51Bx is extracted. Therefore, it is difficult to accurately align the X-ray images P in the integration processing.

The positions of the marker 51Ay and the marker 51By on the proximal end side of each stent substantially coincide with each other. Therefore, in each of the X-ray images P used for generating the integrated image, the marker 51By is included within the range of the region-of-interest R together with the marker 51Ay. As a result, the marker 51By is sometimes extracted by the marker extraction processing. However, since the marker 51Ay and the marker 51By are substantially in the same position, even if the marker 51By is extracted in addition to each of markers 51A from the region-of-interest R, the influence on the enhancement processing of the stent 49A is very small.

In order to accurately align the X-ray images P in the integration processing and acquire an integrated image with the stent 49 A suitably emphasized in a conventional construction, it is necessary to set the region-of-interest R so that the marker 51Bx falls assuredly outside the range of the region-of-interest range. But, it is very difficult to set the range of the region-of-interest R such that each marker 51A falls within the range of the region-of-interest R and the marker 51Bx definitely falls out of the range of the regionof-interest R through the period of the body movement. Therefore, in a conventional configuration, it is very difficult to acquire an integrated image in which the target stent is suitably emphasized in the PCI in the branched blood vessel.

Figure 10:
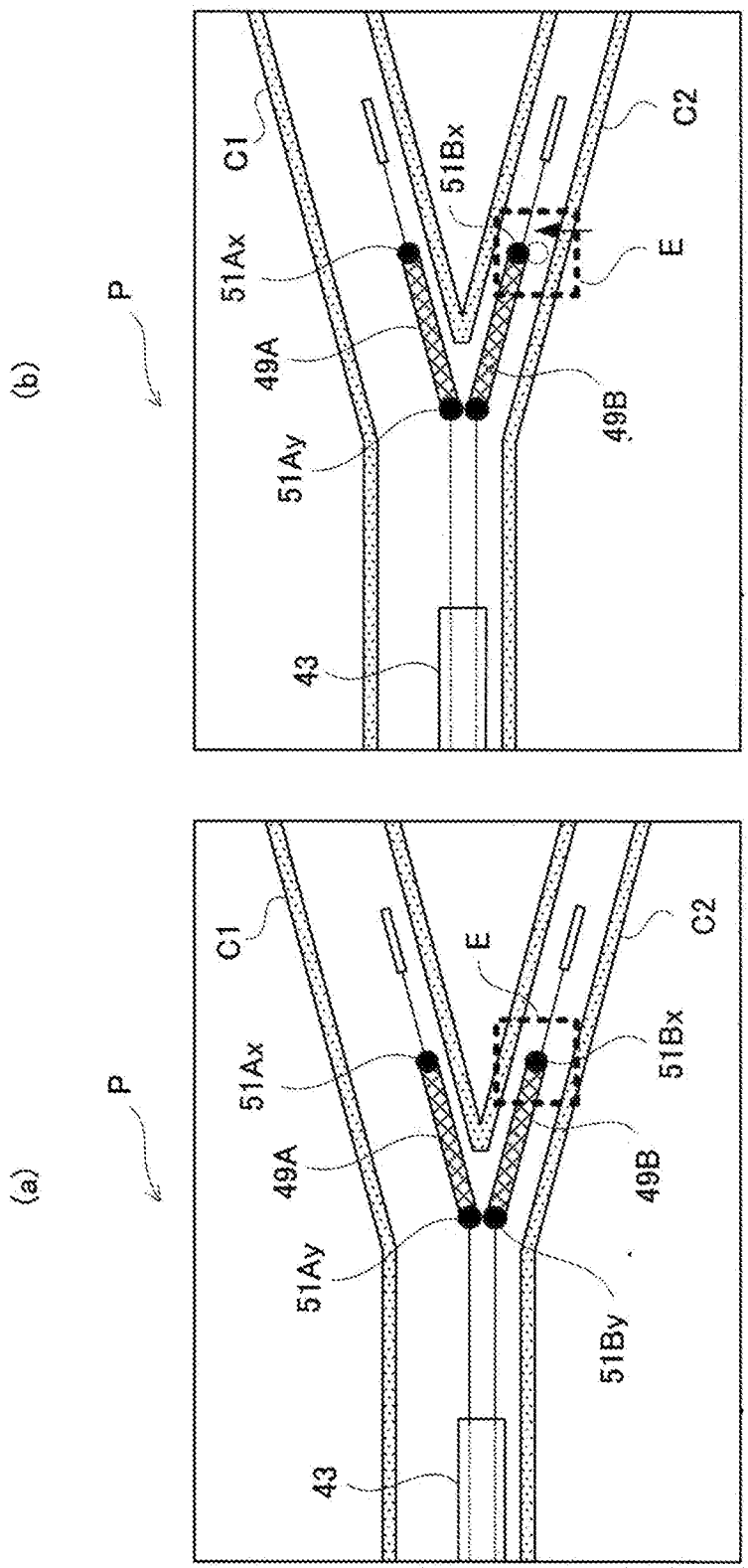
FIG. 10 is a diagram illustrating effects of the configuration of Example 1 in a PCI for branched blood vessels. (a) is an X-ray image in a state in which the exclusion region is set in Example 1, and (b) is an X-ray image in a state in which the marker is displaced by a body movement after setting the exclusion region in Example 1.

On the other hand, in the configuration of Example 1 in which the exclusion region is set, the marker 51Bx can be assuredly excluded from the target of the marker extraction processing by setting the exclusion region E so as to surround the marker 51Bx (FIG. 10 (*a*)). In a conventional configuration, it is necessary to set the region-of-interest R so as to surround each of all the markers 51A, while in the configuration of Example 1, it is sufficient to set the exclusion region E so as to surround only the marker 51Bx.

In such a configuration of Example 1, even cases where the exclusion region E is set to be somewhat wider than the marker 51Bx considering the range which periodically displaces due to body movements, the boundary line of the exclusion region E sufficiently separates from the markers 51 other than the marker 51Bx. Therefore, the marker 51Bx is included within the range of the exclusion region E through the marking period of the subject M, and the markers 51 other than the marker 51Bx is located outside the range of the exclusion region E (FIG. 10 (*b*)). Therefore, in Example 1, it is possible to easily acquire an integrated image in which the target stent 49A is suitably emphasized in the PCI in the branched blood vessel. As a result, in Example 1, using the integrated image high in visibility of the stent, the PCI in the blood vessel branch portion can be proceeded more suitably.

Example 2

Next, Example 2 of the present invention will be described with reference to the drawings. The overall configuration and the operation flow of the X-ray fluoroscopic imaging apparatus according to Example 2 are the same as those of the X-ray fluoroscopic imaging apparatus according to Example 1. However, Example 1 and Example 2 differ from each other in details of the step (Step S3) performing the marker extraction processing using the X-ray image information in the range except for the exclusion region E. That is, in Example 1, as shown in FIG. 6, the image processing for excluding the exclusion region E from the X-ray image P is performed to generate the exclusion processed image Q, and the feature point H is detected from the exclusion processed image Q. Based on the reference parameter of the marker 51, the actual marker 51 is determined from the feature point H.

Figure 11:
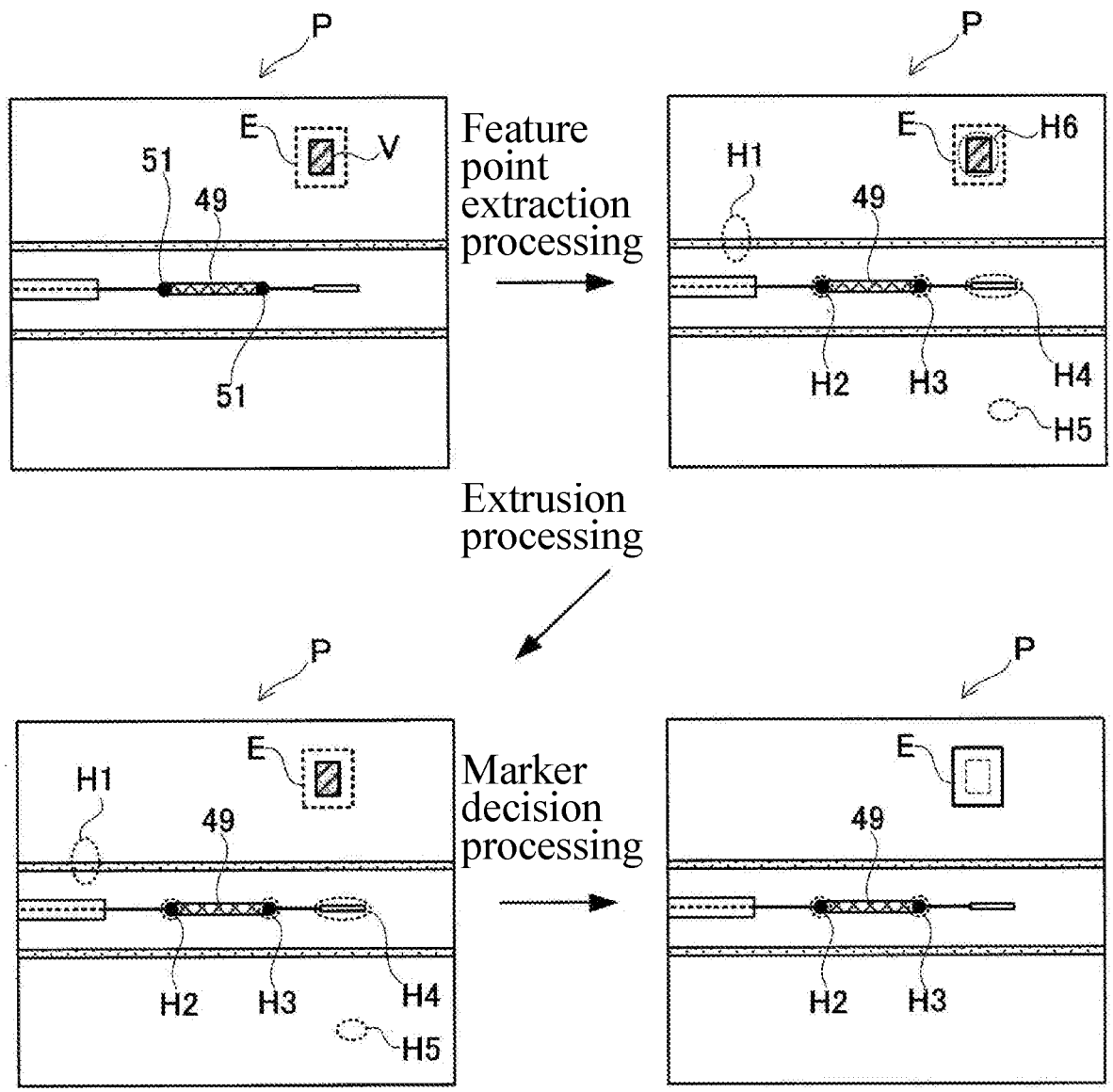
FIG. 11 is a diagram illustrating various kinds of image processing executed in Step S3 of Example 2.

On the other hand, in Example 2, as shown in FIG. 11, the feature point H is detected from the entire X-ray image Q (FIG. 11, upper left) generated by the image generation unit 27 in Step S2 (upper right of FIG. 11). In Example 1, the feature point detection processing is carried out using the exclusion processed image Q in which the obstacle V is excluded, so the feature points H to be detected are feature points H1 to H5 (FIG. 6, lower left). On the other hand, in Example 2, the feature point detection processing is performed using the entire X-ray image P, so that the region corresponding to the obstacle V is detected as the feature point H6 as well as the feature points H to be detected are detected as the feature points H1 to H5.

In Example 2, after detecting the feature points, the processing for extruding the feature point included in the range of the exclusion region E among the detected feature points H is performed (FIG. 11, lower left). Among the feature points H1 to H6, the feature point H6 included in the exclusion region E is excluded by the exclusion processing from the target of the marker determination processing to be performed later. The marker detection unit 31 performs marker determination processing similar to that of Example 1 for each of the feature points H remained after the exclusion processing. Based on various parameter groups that become criteria of the marker 51 by the marker determination processing, the actual markers 51 are specified from the feature points H1 to H5 (FIG. 11, lower right).

When the markers 51 are specified, the marker extraction processing according to Step S3 of Example 2 is completed. Thereafter, the integration unit 33 performs the image processing of aligning the positions of the extracted markers 51 with respect to a predetermined number of X-ray images P as references to generate an integrated image. As described above, Example 2 has a configuration for setting the exclusion region E in the X-ray image in the same manner as in Example 1. The marker extraction unit 31 is configured to extract the markers 51 from the range except for the exclusion region of the X-ray image.

For this reason, by setting the exclusion region E so as to enclose the obstacle V, it is possible to assuredly avoid the obstacle, such as, e.g., a clip and a pacemaker, from being erroneously extracted as a marker. Therefore, even in cases where a surgeon moves a stent or even in cases where a region-of-interest cannot be set appropriately due to a reason that the stent and the obstacle are in close proximity, it is preferable to exclude the obstacle from the marker extraction targets and generate an integrated image. As a result, it is possible to proceed with a PCI more safely using an integrated image with the stent preferentially emphasized.

In Example 1, in the marker extraction processing of Step S3, the marker extraction unit 31 performs exclusion processing, then performs the feature point detection processing, and further performs the marker determination processing. Therefore, in the exclusion processing according to Example 1, the image processing to exclude the image information of the entire exclusion region E among the X-ray images P becomes necessary.

On the other hand, in Example 2, the marker extraction unit 31 performs the feature point detection processing, then performs the exclusion processing, and further performs the marker determination processing. For this reason, in the exclusion processing of Example 2, the image processing for selectively excluding the feature points included within the range of the exclusion region E is performed. Since it is possible to execute the process of excluding the feature point by a simple operation of canceling the state selected as the feature point, in the case of Example 2, the computation processing required for the exclusion processing becomes simpler. As a result, it is possible to shorten the time required for the marker extraction processing in Step S3.

Example 3

Figure 12:
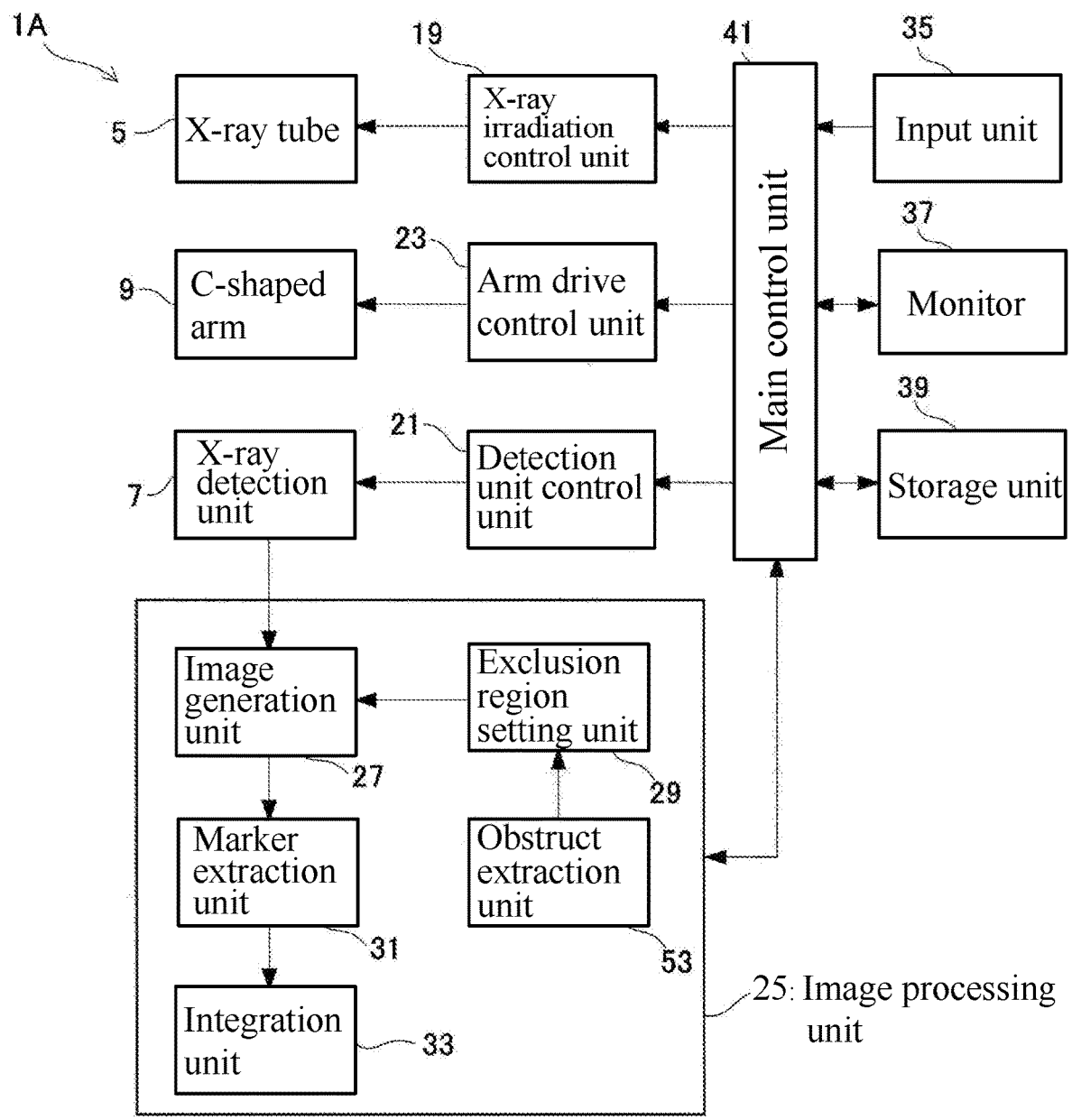
FIG. 12 is a functional block diagram illustrating the configuration of the X-ray fluoroscopic imaging apparatus according to Example 3.

Next, Example 3 of the present invention will be described with reference to the drawings. In Example 3, in addition to the configuration according to Example 1 or Example 2, it is characterized to have a configuration in which the obstacle V which is a radiopaque material other than the marker is extracted from the X-ray image P and an exclusion region E is automatically set. That is, in the X-ray fluoroscopic imaging apparatus 1A according to Example 3, as shown in FIG. 12, the image processing unit 25 further includes an obstacle extraction unit 53. The obstacle extraction unit 53 is provided at the upper stage of the exclusion region setting unit 29 and extracts the obstacle V from the X-ray image generated by the image generation unit 27. In Example 3, the exclusion region setting unit 29 sets a predetermined range including the obstacle V extracted by the obstacle extraction unit 53 as an exclusion region E. The obstacle extraction unit 53 corresponds to the obstacle extraction means in the present invention.

The operation steps of the X-ray fluoroscopic imaging apparatus 1A according to Example 3 are in common with those in Example 1 and Example 2. However, the process of Step S2 according to Example 3 is different from other Examples. Here, as to the steps of Step S2 according to Example 3, the points different from other Examples will be mainly described.

In the step of Step S2 of each of Example 1 and Example 2, a surgeon operates the input unit 35 to manually set the exclusion region E for the X-ray image P generated in Step S1. On the other hand, in Example 3, after the image generation unit 27 generates the X-ray image P in Step S1, an obstacle is first extracted in Step S2. That is, the obstacle extraction unit 53 scans the X-ray image to extract the obstacle V from the X-ray image P.

As an example of the method by which the obstacle extraction unit 53 extracts the obstacle, a method can be exemplified in which the information of the obstacle stored in advance in the storage unit 39 is referred and the obstacle V is extracted from the X-ray image P by image processing such as pattern matching. Since the configuration that can be an obstacle V is limited to some extent, such as, e.g., a pacemaker and a clip, it is relatively easy to store pattern information, such as, e.g., a shape of a candidate of the obstacle V in advance. Note that a method in which the obstacle extraction unit 53 extracts the obstacle is not limited to pattern matching, and other known methods may be used. The information on the position and/or the range of the obstacle V extracted by the obstacle extraction unit 53 is transmitted from the obstacle extraction unit 53 to the exclusion region setting unit 29.

After the extraction of the obstacle V, setting of the exclusion region is performed. That is, the exclusion region setting unit 29 sets the exclusion region E so as to surround the obstacle V based on the information of the obstacle V extracted by the obstacle extraction unit 53. It is preferable to set the range of the exclusion region E so that the obstacle V always falls within the range of the exclusion region E, taking into consideration the range of the periodic movements due to the body movements of the subject M. After the exclusion region E is automatically set, the surgeon may manually add, delete, or change the exclusion region E by manipulating the input unit 35 as appropriate.

After setting the exclusion region E, the marker is extracted from the range of the X-ray image except for the exclusion region (Step S3) in the same manner as in other Examples. Then, with reference to the position of the extracted marker as a reference, the integration processing is performed on a predetermined number of X-ray images P generated most recently to generate an integrated image (Step S4). Referring to the integrated image in which the stent is subjected to the enhancement processing, a surgeon places the stent in an appropriate position (Step S5).

As described above, the X-ray fluoroscopic imaging apparatus 1A according to Example 3 is provided with the obstacle extraction unit 53, so that the exclusion region setting unit 29 can automatically set the exclusion region E so as to surround the obstacle V in Step S2. Therefore, since the time required for setting the exclusion region according to Step S2 can be greatly shortened, the burden on the surgeon at the time of the PCI can be further reduced.

The present invention is not limited to the aforementioned embodiments, and can be modified as follows.

Figure 13:
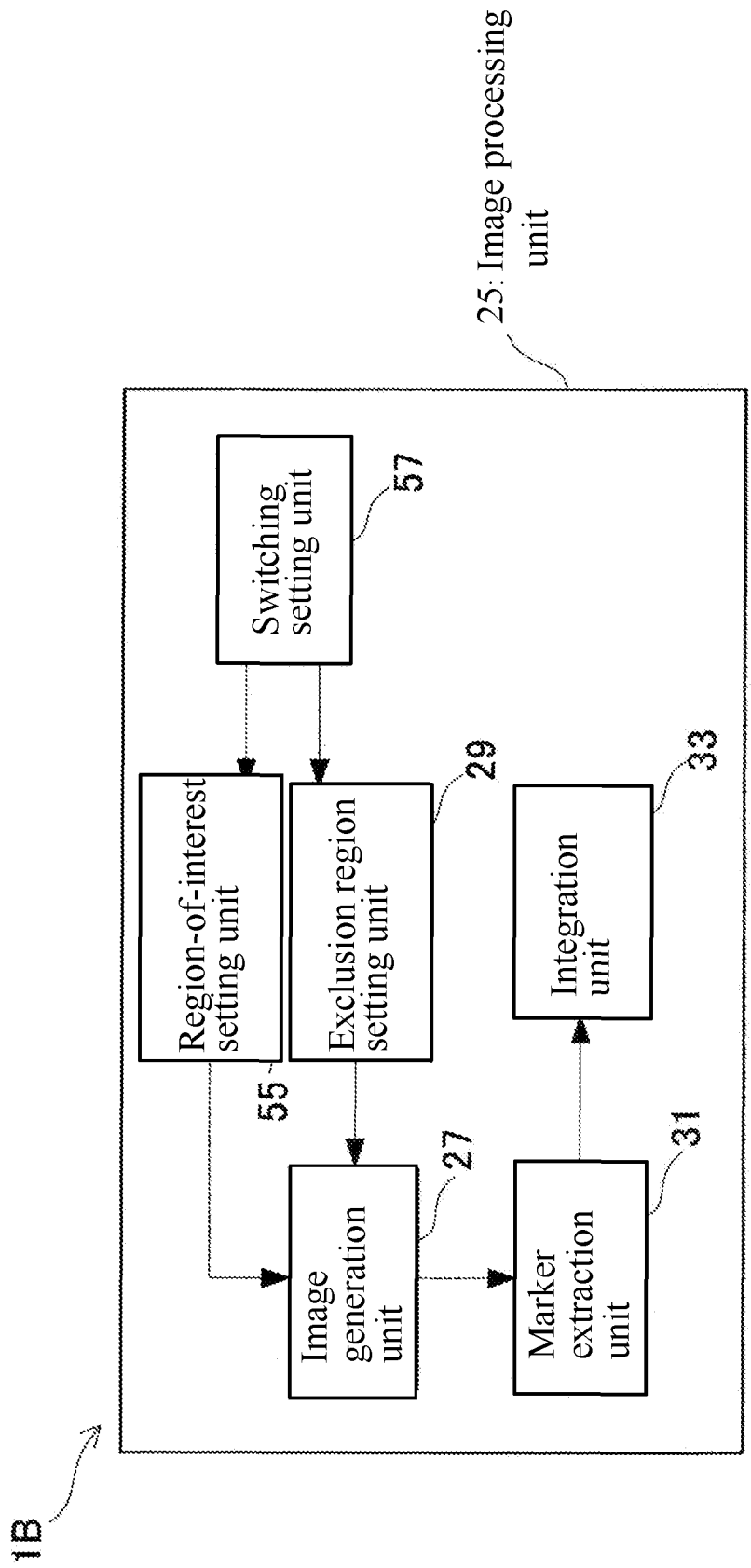
FIG. 13 is a functional block diagram illustrating a configuration of the image processing unit according to a modified example.

(1) In each of the above-described Examples, a configuration may be adopted in which the state of setting the exclusion region and the state of setting the region-of-interest are appropriately switched. In the X-ray fluoroscopic imaging apparatus 1B according to such a modification, the image processing unit 25 is further provided with a region-of-interest setting unit 55 and a switching setting unit 57 as shown in FIG. 13. The region-of-interest setting unit 55 sets the region-of-interest in the X-ray image according to the instruction content to be input to the input unit 35. The switching setting unit 57 is provided at the upper stage of the exclusion region setting unit 29 and the region-of-interest setting unit 55, and switches the ON/OFF state of the exclusion region setting unit 29 and the region-of-interest setting unit 55 as necessary according to the instruction content to be input to the input unit 35. Note the region-of-interest setting unit 55 corresponds to the region-of-interest setting means in the present invention. Also note that the switching setting unit 57 corresponds to the switching setting means in the present invention.

Figure 14:
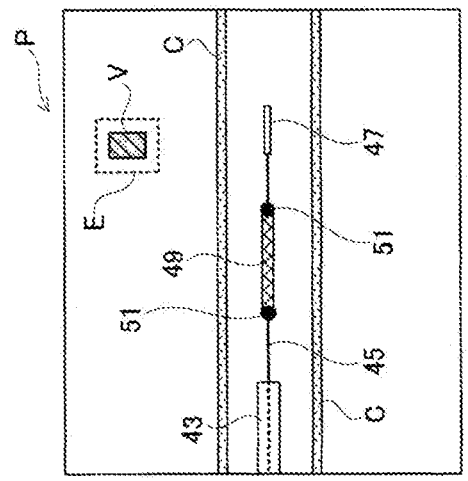
FIG. 14 is a diagram illustrating the operation of Step S2 according to a modified Example. (a) is a view illustrating a case in which the exclusion region setting unit is switched to an ON-state, and (b) is a diagram illustrating a case in which the region-of-interest setting unit is switched to an On-state.
Figure 14:
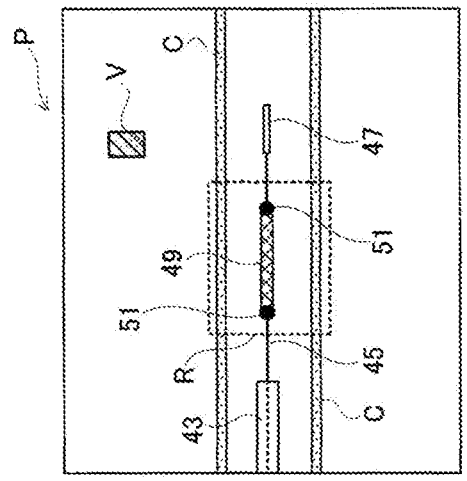
Figure 14:
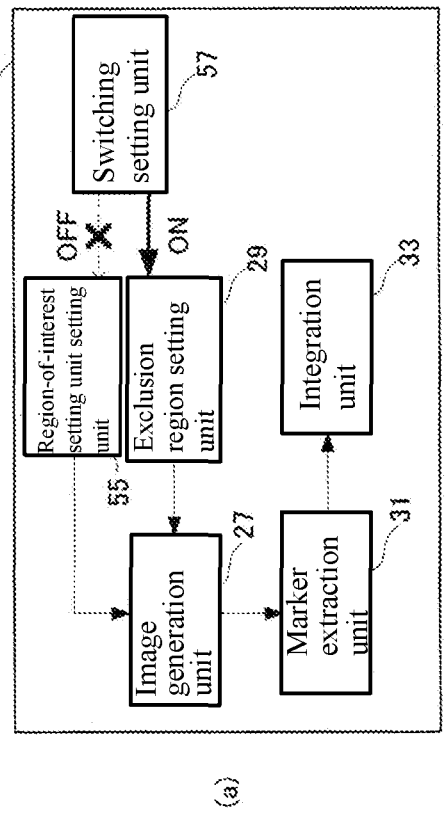
Figure 14:
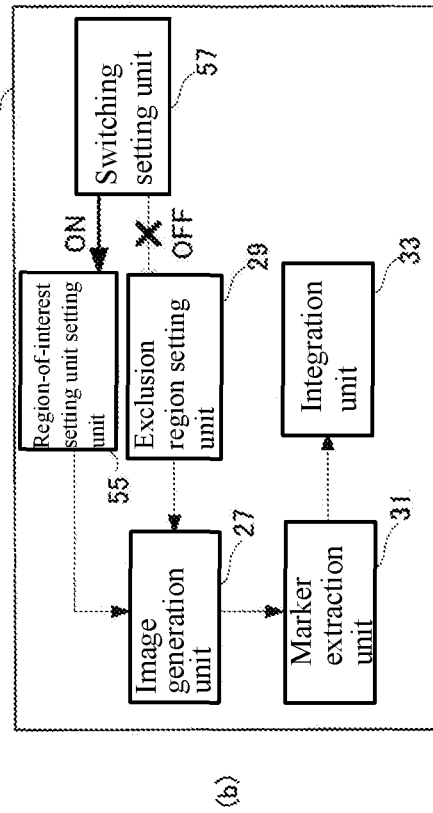
Figure 15:
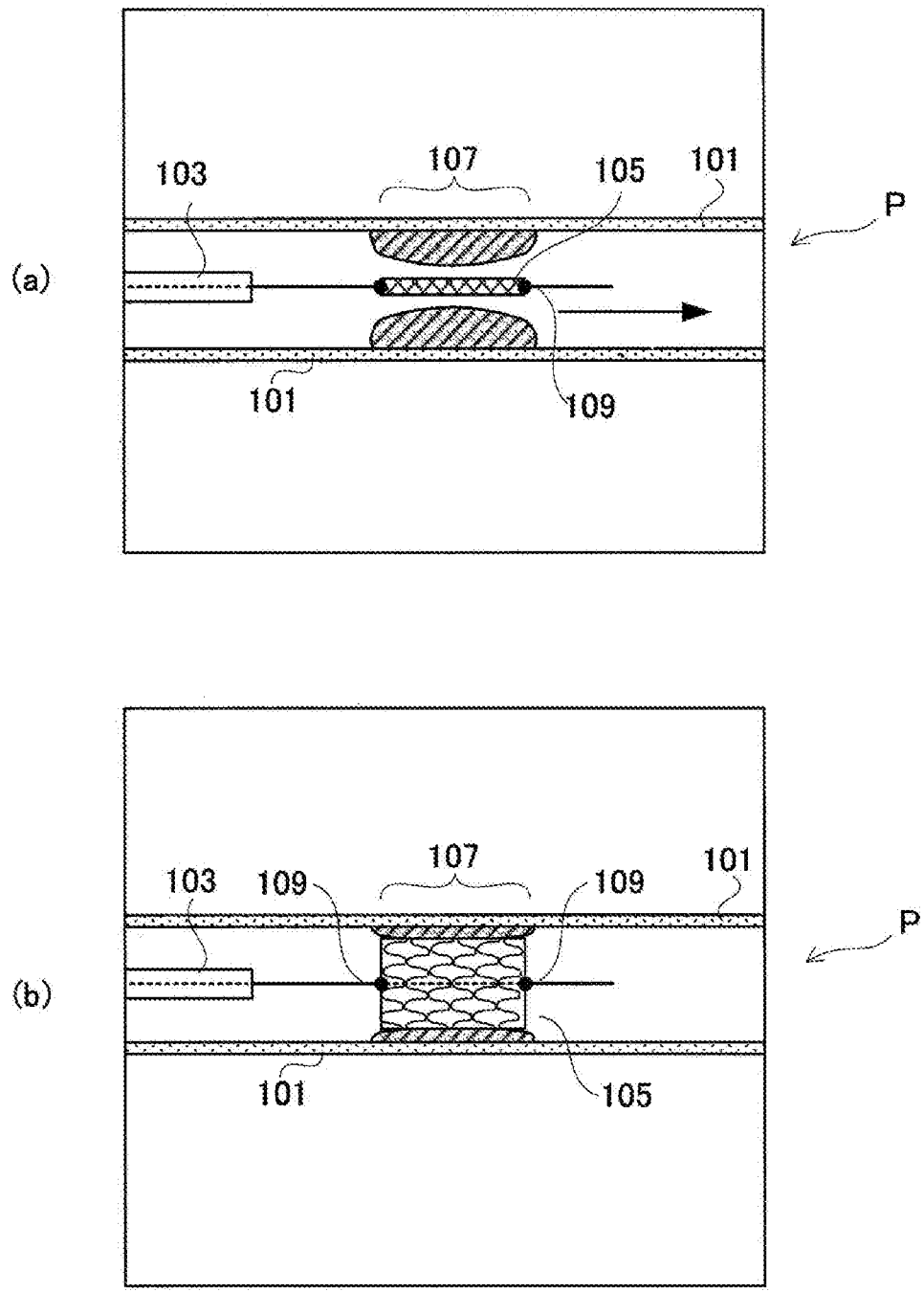
FIG. 15 is a diagram illustrating a process of an interventional treatment according to a conventional example. (a) is a view illustrating a process of causing a stent to reach a strictured segment, and (b) is a view illustrating a process of placing an expanded stent in a strictured segment.

When setting an exclusion region in such a modified Example, a surgeon operates a changeover switch provided in the input unit 35 as an example to set the exclusion region setting to the ON state. In this case, the switching setting unit 57 makes the exclusion region setting unit 29 in the ON state according to the contents of the operation, and makes the region-of-interest setting unit 55 in the OFF state (left drawing of FIG. 14 (*a*)). The state in which the exclusion region setting unit 29 is in the ON state and the region-of-interest setting unit 55 is in the OFF state corresponds to the first state in the present invention.

When the exclusion region setting unit 29 becomes the ON state, the region set in the X-ray image P by the operation of the input unit 35 becomes the exclusion region E. In this case, in Step S2, a surgeon draws a boundary line so as to surround the obstacle V and sets the exclusion region E (right drawing in FIG. 14 (*a*)). In the same manner as in each Example, the marker extraction unit 31 extracts the marker 51 from the range except for the exclusion region E in the X-ray image P in Step S3.

On the other hand, when setting the region-of-interest, a surgeon operates the changeover switch provided in the input unit 35 as an example to make the region-of-interest setting in the ON state. In this case, the switching setting unit 57 makes the exclusion region setting unit 29 in the OFF state according to the contents of the operation, and makes the region-of-interest setting unit 55 in the OFF state (left drawing in FIG. 14 (*a*)). The state in which the exclusion region setting unit 29 is in the OFF state and the region-of-interest setting unit 55 is in the ON state corresponds to the second state in the present invention.

When the region-of-interest setting unit 55 becomes the ON state, the region set in the X-ray image P by the operation of the input unit 35 becomes the region-of-interest R. In this case, in Step S2, a surgeon draws a boundary line so as to surround each of the markers 51 and sets the region-of-interest R (right drawing in FIG. 14 (*a*)). In the same manner as in the conventional configuration according to Patent Document 2, in Step S3, the marker extraction unit 31 extracts the markers 51 from the range within the region-of-interest R of the X-ray image P.

In the configuration according to the modified Example, the state of setting setting the exclusion region and the state of setting the region-of-interest is switched by the switching setting unit 57 as appropriate. In the state in which the region-of-interest is set (second state), the marker is extracted from the range of the region-of-interest range in the X-ray image. That is, in the state of setting the region-of-interest, the range of the X-ray image to be subjected to the marker extraction processing is limited within the range of the region-of-interest R surrounding each of the markers. On the other hand, the range of the X-ray image to be subject to the marker extraction processing in the state of setting the exclusion region is the entire range of the X-ray image except for the exclusion region E surrounding the obstacle V.

In general, since the range of region-of-interest R is narrower than the entire range of the X-ray image P except for the exclusion region E, in the state of setting the region-of-interest, the operation required for the marker extraction processing becomes simpler. Therefore, by adopting the configuration provided with the switching setting unit 57, in cases where the stent 49 and the obstacle V are separated, the time required for the marker extraction processing can be shortened as the state of setting the region-of-interest.

On the other hand, as shown in FIG. 8 (c) and FIG. 10, in cases where the obstacle V cannot be suitably excluded from the subject of the marker extraction processing unless the exclusion region is set, the exclusion region is switched to the state of setting the exclusion region (first state) to obtain an integrated image in which the stent 49 is more preferably emphasized. That is, in the configuration according to the modified Example, it is possible to acquire an integrated image preferably subjected to the enhancement processing under the condition in which it was conventionally difficult to acquire a suitably integrated image by switching the region-of-interest set situation and the exclusion region set state depending on the situation while shortening the required time of the PCI.

(3) In each Example described above, the integration unit 33 is configured to display the integrated image S on the monitor 37, but it is not limited to this. That is, after generating the integrated image S, the integration unit 33 may be configured to further perform cutout processing to cut out the vicinity of the stent 49 from the integrated image S and enlarge the image of the neighborhood region of the extracted stent 49 appropriately to display the enlarged image on the monitor 37. The enlarged image subjected to the cutout processing and the enlargement processing is further improved in the visibility of the stent 49. Therefore, by referring to the enlarged image, a surgeon can proceed with the PCI more favorably.

Alternatively, after generating the integrated image S using the X-ray images Pa to Pd, it may be configured such that the real-time X-ray image Pa and the integrated image S (or the enlarged image) generated most recently are displayed in parallel on the monitor 37. In this case, since a surgeon can refer to the integrated image image S higher in visibility and the X-ray image Pa with more real time property at the same time, it is possible to proceed with the PCI more suitably and hold the stent at the exact position.

(4) In each of the above-described Examples, the description is made using the catheter system provided with a stent as a device. However, as a configuration of the device with which the catheter system is provided, a rotor blender used for atherectomy may be exemplified other than the stent.

(5) In each Example described above, the configuration in which the X-ray tube 5 and the X-ray detector 7 are provided at the C-shaped arm 9 is adopted in the above Examples, but the X-ray fluoroscopic imaging apparatus 1 is not limited to the configuration having the C-shaped arm 9. That is, in place of the C-shaped arm 9, it may be configured such that the X-ray tube support portion suspended from the ceiling supports the X-ray tube 5.

DESCRIPTION OF REFERENCE SYMBOLS

1: X-ray fluoroscopic imaging apparatus
5: X-ray tube
7: X-ray detector
17: collimator
27: image generation unit
29: exclusion region setting unit (exclusion region setting means)
31: marker extraction unit (marker extraction means)
33: integration unit
35: input unit
37: monitor
39: storage unit
40: main control unit
49: stent (device)
51: marker
53: obstacle extraction unit (obstacle extraction means)
55: region-of-interest setting unit (region-of-interest setting means)
57: switching setting unit (switching setting means)

The invention claimed is:

1. An X-ray fluoroscopic imaging apparatus comprising:
an X-ray tube configured to irradiate an X-ray to a subject;
an X-ray detector configured to detect the X-ray that has transmitted through the subject;
an image generation unit configured to generate an X-ray image of a region including a device, with one or more radiopaque markers, being operated by an operator at the time of the operation to be inserted into a body of the subject by using a detection signal output from the X-ray detector;
exclusion region setting means configured to set a boundary line based on an operation by an operator to surround a region in the X-ray image that includes a radiopaque material object different from any of the device being operated by the operator at the time of the operation and the one or more radiopaque markers of the device, and set an inner region of the boundary line as an exclusion region in the X-ray image;
marker extraction means configured to extract the one or more radiopaque markers of the device from a range outside the exclusion region in the X-ray image; and
an integration unit configured to generate an integrated image by superimposing a plurality of the X-ray images based on a position of the one or more radiopaque markers extracted by the marker extraction means.

2. The X-ray fluoroscopic imaging apparatus as recited in claim 1,
further comprising exclusion processed image generation means configured to generate an exclusion processed image by removing the range of the exclusion region from the X-ray image,
wherein the marker extraction means extracts the one or more radiopaque markers from the exclusion processed image.

3. The X-ray fluoroscopic imaging apparatus as recited in claim 1, wherein
the marker extraction means detects a candidate of the one or more radiopaque markers as a feature point from the X-ray image and excludes the feature point included within the range of the exclusion region from the candidate of the one or more radiopaque markers, and then identifies the one or more radiopaque markers from the feature point included in the range outside the exclusion region to extract the one or more radiopaque markers of the device from the range outside the exclusion region in the X-ray image.

4. The X-ray fluoroscopic imaging apparatus as recited in claim 1,
further comprising obstacle extraction means configured to extract a radiopaque object different from any of the one or more radiopaque markers and the device being operated by the operator at the time of the operation as an obstacle from the X-ray image,
wherein the exclusion region setting means sets the exclusion region so as to surround the obstacle extracted by the obstacle extraction means.

5. The X-ray fluoroscopic imaging apparatus as recited in claim 1, further comprising:
region-of-interest setting means configured to set a region-of-interest in the X-ray image; and
switching setting means configured to switch between a first state in which the exclusion region setting means is in an ON state and a second state in which the region-of-interest setting means is in an ON state,
wherein the marker extraction means extracts the one or more radiopaque markers from the X-ray image except for the exclusion region in the first state, and extracts the one or more radiopaque markers from within the range of the region-of-interest in the X-ray image in the second state.

\* \* \* \* \*